United States Patent

(12) United States Patent
Gavardinas et al.

(10) Patent No.: US 7,803,814 B2
(45) Date of Patent: Sep. 28, 2010

(54) TRICYCLIC STEROID HORMONE NUCLEAR RECEPTOR MODULATORS

(75) Inventors: Konstantinos Gavardinas, Monrovia, IN (US); Jonathan Edward Green, Avon, IN (US); Prabhakar Kondaji Jadhav, Zionsville, IN (US); Donald Paul Matthews, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1027 days.

(21) Appl. No.: 10/576,761

(22) PCT Filed: Dec. 8, 2004

(86) PCT No.: PCT/US2004/038233

§ 371 (c)(1),
(2), (4) Date: Apr. 21, 2006

(87) PCT Pub. No.: WO2005/066161

PCT Pub. Date: Jul. 21, 2005

(65) Prior Publication Data

US 2007/0037788 A1    Feb. 15, 2007

Related U.S. Application Data

(60) Provisional application No. 60/531,283, filed on Dec. 19, 2003.

(51) Int. Cl.
*A61K 31/445* (2006.01)
*C07D 401/14* (2006.01)

(52) U.S. Cl. ...................... 514/320; 546/196
(58) Field of Classification Search .............. 514/320; 546/196
See application file for complete search history.

(56) References Cited

U.S. PATENT DOCUMENTS 4,999,363 A    3/1991    Oshima et al.
5,024,912 A    6/1991    Neishi et al.
5,093,210 A    3/1992    Ohta et al.

FOREIGN PATENT DOCUMENTS

| JP | 01161245 | 6/1989 |
|---|---|---|
| JP | 04046352 | 2/1992 |
| WO | WO99/33786 | 7/1999 |
| WO | WO 00/59884 | 10/2000 |
| WO | WO 03/053358 | 7/2003 |
| WO | WO 03/078394 | 9/2003 |
| WO | WO 2004/052847 | 6/2004 |

OTHER PUBLICATIONS

Cheng, et al, "Synthesis and Structure-Activity Relationships of 9-Substituted Acridines as Endothelin-A Receptor Antagonists," *Bioorganic and Medicinal Chemistry Letters*, vol. 6, No. 24, pp. 2999-3002 (1996).

*Primary Examiner*—Rebecca L Anderson
(74) *Attorney, Agent, or Firm*—Alexander Wilson

(57) ABSTRACT

The present invention provides a compound of the formula (I): or a pharmaceutically acceptable salt thereof; pharmaceutical compositions comprising an effective amount of a compound of Formula (I) in combination with a suitable carrier, diluent, or excipient; and methods for treating physiological disorders, particularly congestive heart disease, hypertension, rheumatoid arthritis or inflammation, comprising administering to a patient in thereof an effective amount of a compound of Formula (I).

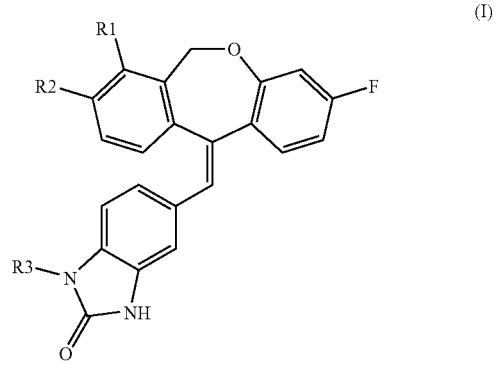

15 Claims, No Drawings

TRICYCLIC STEROID HORMONE NUCLEAR RECEPTOR MODULATORS

This application is the national phase application, under 35 USC §371, for PCT/US2004/038233, filed 8 Dec. 2004, which claims the benefit under 35 USC §119(e) of U.S. provisional application 60/531,283, filed 19 Dec. 2003.

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid-receptor (MR), the estrogen receptor (ER), and the progesterone receptor (PR). Tenbaum et al., Int. J. Biochem. Cell. Bio., 29(12):1325-1341 (1997).

In contrast to membrane bound receptors, nuclear hormone receptors encounter their respective ligands following entry of the ligand into the dell. Once ligand binding occurs, the ligand-receptor complex modulates transcription of target genes within the cell nucleus. For example, most ligand-free nuclear receptors are bound in a complex with heat shock proteins (HSPs) in the cytoplasm. Following entry of circulating hormone into the cell, binding elicits a conformational change in the receptor, dissociating the receptor from the hsp. The ligand bound receptors translocate to the nucleus, where they as monomers as well as hetero- and homodimers in binding to particular hormone response elements (HREs) in the promoter regions of target genes. The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of HSPs and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Mineralocorticoids and glucocorticoids exert profound influences on a multitude of physiological functions by virtue of their diverse roles in growth, development, and maintenance of homeostasis. The actions are mediated by the MR and GR which share approximately 94% homology in their respective DNA binding regions, and approximately 57% homology in their respective ligand-binding domains. Kino et al., J. of Endocrinology, 169, 437-445 (2001). In visceral tissues, such as the kidney and the gut, MR regulates sodium retention, potassium excretion, and water balance in response to aldosterone. In addition, MR expression in the brain appears to play a role in the control of neuronal excitability, in the negative feedback regulation of the hypothalamic-pituitary-adrenal axis, and in the cognitive aspects of behavioral performance. Castren et al., J. of Neuroendocrinology, 3, 461-466 (1993). GR, which is ubiquitously expressed in almost all tissues and organ systems, is crucial for the integrity of central nervous system function and the maintenance of cardiovascular, metabolic, and immune homeostasis. Kino et al., J. of Endocrinology, 169, 437-445 (2001).

Elevations in aldosterone levels, or excess stimulation of mineralocorticoid receptors, are linked to several physiological disorders or pathologic disease states including, Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. Hadley, M. E., ENDOCRINOLOGY, 2$^{nd}$ Ed., pp. 366-381, (1988); and Brilla et al., Journal of Molecular and Cellular Cardiology, 25 (5), pp. 563-575 (1993). Additionally, elevated aldosterone levels have been increasingly implicated with congestive heart failure (CHF). In CHF, the failing heart triggers hormonal mechanisms in other organs in response to the attending reductions in blood flow and blood pressure seen with CHF. In particular, the kidney activates the renin-angiotensin-aldosterone system (RAAS) causing an increase in aldosterone production by the adrenals which, in turn, promotes water and sodium retention, potassium loss, and further edema. Although historically it was believed that aldosterone participated in the etiology of CHF only as a result of its salt retaining effects, several recent studies have implicated elevated aldosterone levels with events in extra-adrenal tissues and organs, such as myocardial and vascular fibrosis, direct vascular damage, and baroreceptor dysfunction. Pitt et al., New Eng. J. Med., 341:709-717 (1999). These findings are particularly significant since angiotensin converting enzyme (ACE) inhibitors, which were once thought to completely abolish aldosterone production, are now believed to only transiently suppress aldosterone production which has been shown to occur in extra-adrenal tissues including the heart and vasculature. Weber, New Eng. J. Med., 341:753-755 (1999); Fardella and Miller, Annu. Rev. Nutr., 16:443-470 (1996).

The involvement of aldosterone acting via MR in CHF was confirmed in the recently completed RALES (Randomized Aldactone Evaluation Study) study. Pitt et al., New Eng. J. Med., 341:709-717 (1999). The RALES study demonstrated that the use of Aldactone™ (spironolactone), a well-known competitive MR antagonist, in combination with standard CHF therapy, reduced cardiac related mortality by 30% and frequency of hospitalization by 35% in patients suffering from advanced CHF. However, spironolactone therapy has also been associated with attending side effects such as gastric bleeding, diarrhea, azotemia, hyperchloremic metabolic acidosis an type-4 renal tubule acidosis, nausea, gynecomastia, erectile dysfunction, hyperkalemia, and irregular menses. Thus, the mineralocorticoid receptor represents a viable target for CHF therapy either alone or in combination with conventional CHF therapies such as vasodilators (ACE inhibitors), inotropics (digoxin), diuretics, or beta blockers. Molecules, preferably non-steroids, which bind to the mineralocorticoid receptor and modulate receptor activity without the attending side effects of current therapies would be particularly desirable.

Finally, published international PCT application WO 02/17895 discloses that aldosterone antagonists are useful in the treatment of subjects suffering from one or more cognitive dysfunctions including, but not limited to psychoses, cognitive disorders (such as memory disturbances), mood disorders (such as depression and bipolar disorder), anxiety disorders, and personality disorders.

Glucocorticoids (e.g. cortisol, corticosterone, and cortisone), and the glucocorticoid receptor, have also been implicated in the etiology of a variety of physiological disorders or pathologic disease states. For example, cortisol hyposecretion is implicated in the pathogenesis of Addison's Disease and may result in muscle weakness, increased melanin pigmentation of the skin, weight loss, hypotension, and hypoglycemia. On the other hand, excessive or prolonged secretion of glucocorticoids has been correlated to Cushing's Syndrome and may also result in obesity, hypertension, glucose intolerance, hyperglycemia, diabetes mellitus, osteoporosis, polyuria, and polydipsia. Hadley, M. E., ENDOCRINOLOGY, $2^{nd}$ Ed., pp. 366-381, (1988). Further, U.S. Pat. No. 6,166, 013, issued Dec. 26, 2000, discloses that GR selective agents could modulate GR activity and, thus, be useful in the treatment of inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome. U.S. Pat. No. 6,166,013 also discloses that GR modulators are especially useful in disease states involving systemic inflammation such as inflammatory bowel disease, systemic lupus erythematosus, polyartitis nodosa, Wegener's granulomatosis, giant cell arthritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis; and that GR modulating compounds have been used as immunostimulants, repressors, and as wound healing and tissue repair agents.

In addition, U.S. Pat. No. 6,166,013 also discloses that GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma.

Thus, it is clear that a ligand which has affinity for steroid hormone nuclear receptors, and particularly for MR and/or GR, could be used to modulate (i.e. repress, antagonize, agonize, partially antagonize, partially agonize) receptor activity and target gene expression, thereby influencing a multitude of physiological functions related to alterations in steroid hormone levels and/or steroid hormone receptor activity. In this regard, such ligands could be useful to treat a wide range of physiological disorders susceptible to steroid hormone nuclear receptor modulation.

Several art references disclose tricyclic-derivative molecules useful as, inter alia, photographic coupling and developing agents, thromboxane A2 modulators, and as histamine H2 antagonists. Further, tricyclic-derivative compounds have also been disclosed as having pharmacological utility as, inter alia, antidepressants and anti-inflammatory agents. Surprisingly, however, and in accordance with the present invention, applicants have discovered a series of tricyclic compounds, particularly benzimidazolone derivatives, with affinity for the mineralocorticoid and/or glucocorticoid receptors. Such compounds could modulate MR or GR activity and, thus, have utility in the treatment of disorders related to alterations in mineralocorticoid or glucocorticoid hormone level and/or to alterations in MR or GR activity. As a further embodiment, the present invention also provides a novel series of novel non-steroidal tricyclic compounds that exhibit MR or GR affinity and modulating activity. Such methods and compounds could address a long felt and continuing need for safe and effective pharmaceutical interventions without the attending side effects of steroidal-type agents. The treatment of hormone related disorders is hereby furthered.

The following references describe examples of the state of the art as it relates to the present invention.

U.S. Pat. No. 5,024,912 discloses 5H Dibenzo (A,D) cycloheptenylidene and 5H Dibenzo (A,D) cycloheptanylidene derivatives as electrophotographic photosensitive agents.

U.S. Pat. Nos. 4,741,976, 4,539,507, 5,093,210, and 5,166, 022 disclose the use of tricyclic molecules in electroluminescent devices.

U.S. Pat. No. 4,282,233 discloses tricyclic molecules (i.e. Loratadine (Claritin™) as H2 antagonists.

U.S. Pat. No. 4,999,363 (and family members) discloses tricyclic molecules as thromboxane A2 antagonists.

U.S. Pat. Nos. 5,378,701 and 5,478,840 and 5,607,955 disclose tricyclic molecules as angiotensin II antagonists.

U.S. Pat. No. 6,362,188 B1 discloses tricyclic molecules as farnesyl protein transferase inhibitors.

Published International PCT Application WO 99/33786 discloses tricyclic propanamide derivative molecules as anti-inflammatory agents. Published International PCT Application WO 96/19458 and U.S. Pat. Nos. 5,696,130; 5,994,544; 6,017,924, and 6,121,450 disclose quinoline derivative analogs as steroid hormone receptor modulators.

Co-pending International PCT Application PCT/US03/16213 discloses a genus of tricyclic derivative compounds functional as nuclear hormone receptor modulators, particularly MR and GR modulators.

Published International PCT Application WO 00/05984 discloses tricyclic derivatives as antiparasitic agents.

SUMMARY OF THE INVENTION

The present invention is directed to the discovery that a novel genus of tricyclic molecules, within the scope of Co-pending International PCT Application PCT/US03/16213, and as defined below, are modulators of steroid hormone nuclear receptors and, therefore, may have utility as pharmaceutical agents. Accordingly, the present invention provides a compound of the formula:

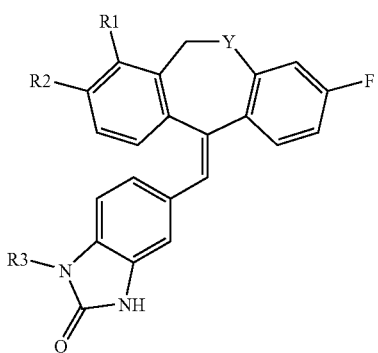

Formula I wherein,

Y represents $CH_2$ or O;

R1 and R2 each independently represent hydrogen or fluoro

R3 represents a group of the formula:

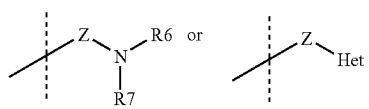

wherein Z represents $(CH_2)_n$ or $-CR4R5-CH_2-$;

n represents 0-3; and

Het represents a group of the formula:

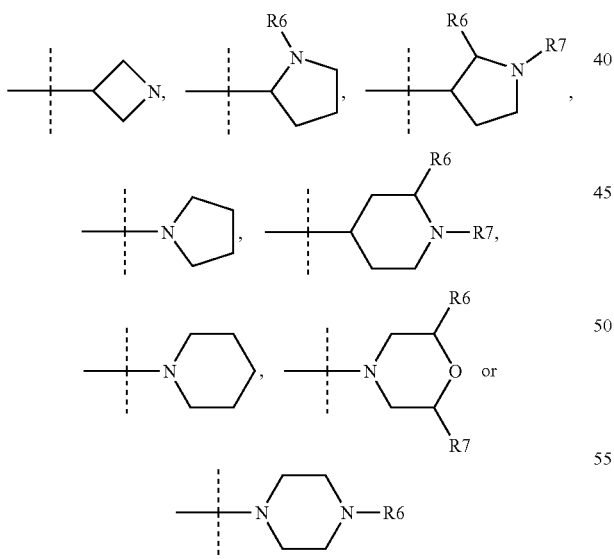

R4 and R5 each independently represent at each occurrence hydrogen or methyl;

R6 and R7 each independently represent at each occurrence hydrogen, methyl, or ethyl;

provided Formula I does not represent a compound selected from the group consisting of

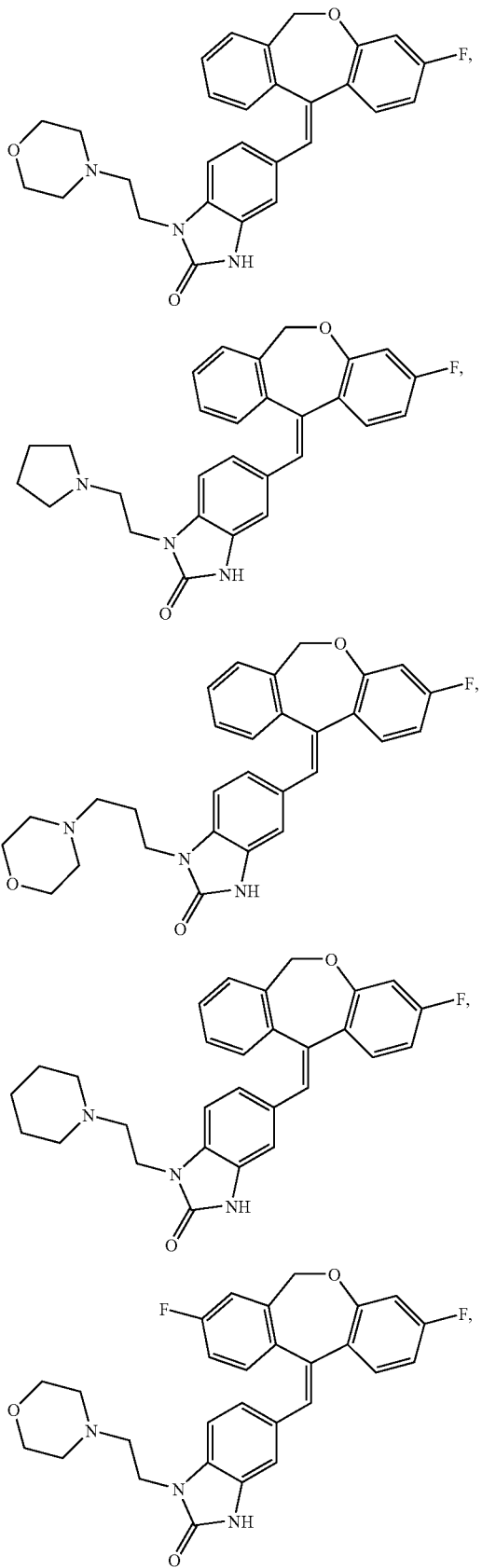

-continued

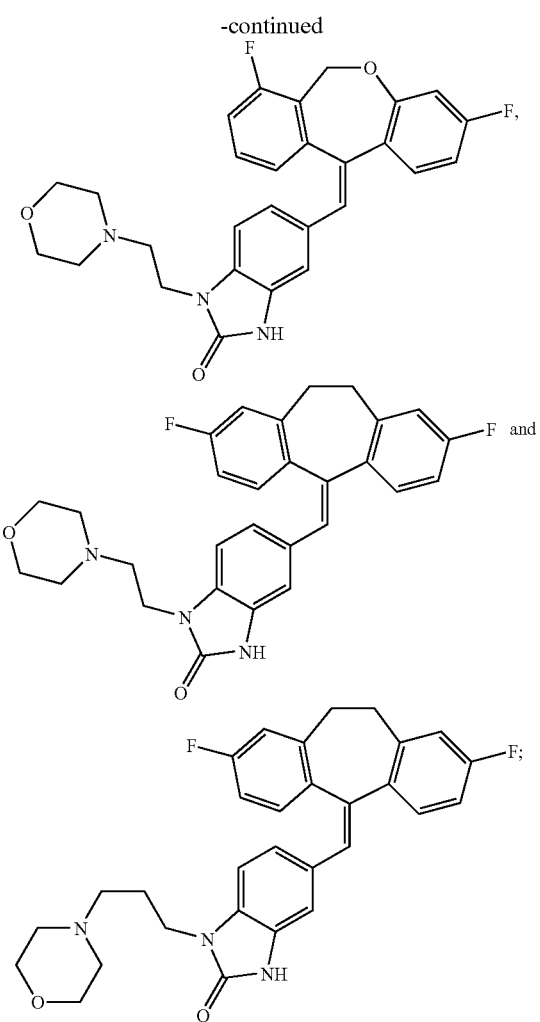

or a pharmaceutically acceptable salt thereof.

As another aspect, the present invention provides a method of treating a physiological disorder susceptible to steroid hormone nuclear receptor modulation comprising administering to a patient in need thereof an effective amount of a compound of Formula I as described herein and above. Examples of such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As a further aspect, the present invention provides a method of treating a physiological disorder susceptible to mineralocorticoid or glucocorticoid receptor modulation comprising administering to a patient in need thereof an effective amount of a compound of Formula I as described herein and above. As a more particular aspect, the present invention provides a method of treating a physiological disorder susceptible to mineralocorticoid or glucocorticoid receptor antagonism comprising administering to a patient in need thereof an effective amount of a compound of Formula I. As an even more particular aspect the present invention provides a method of treating hypertension (isolated systolic and combined systolic/diastolic), systolic and/or diastolic congestive heart failure, rheumatoid arthritis or inflammation comprising administering to a patient in need thereof an effective amount of a compound of Formula I as described herein and above.

As a separate aspect, the present invention also provides a method of modulating a steroid hormone nuclear receptor comprising contacting said receptor with an effective amount of a compound of Formula I. More particularly, the present invention provides a method of modulating the mineralocorticoid or glucocorticoid receptor comprising contacting said receptor with an effective amount of a compound of Formula I. More particularly still, the present invention provides a method of antagonizing the mineralocorticoid or glucocorticoid receptor comprising contacting said receptor with an effective amount of a compound of Formula I, as described herein and above.

In addition, the present invention provides pharmaceutical compositions of compounds of Formula I, including any pharmaceutically acceptable salts and hydrates thereof, comprising a compound of Formula I in combination with a pharmaceutically acceptable carrier, diluent or excipient. This invention also encompasses novel intermediates, and processes for the synthesis of the compounds of Formula I.

The present invention also provides the use of a compound of Formula I, or a pharmaceutically acceptable salt thereof, for the manufacture of a medicament for treating a physiological disorder susceptible to steroid hormone nuclear receptor modulation. More particularly, the present invention provides the use of a compound of Formula I, or a pharmaceutically acceptable salt thereof, for the manufacture of a medicament for treating hypertension, congestive heart failure, rheumatoid arthritis or inflammation.

DETAILED DESCRIPTION OF THE INVENTION

The present invention provides compounds of Formula I with affinity for steroid hormone nuclear receptors, particularly MR and/or GR, which could be used to modulate (i.e. repress, antagonize, agonize, partially antagonize, partially agonize) nuclear receptor activity and target gene expression, thereby influencing physiological functions related to steroid hormone levels and/or steroid hormone receptor activity. In this regard, compounds of Formula I are believed to be useful in treating or preventing a multitude of physiological disorders susceptible to steroid hormone nuclear receptor modulation. Thus, methods for the treatment or prevention of physiological disorders susceptible to steroid hormone nuclear receptor modulation constitute another important embodiment of the present invention. As a particular aspect, the present invention provides compounds useful as mineralocorticoid or glucocorticoid receptor modulators. As a more particular aspect, the present invention provides compounds useful as mineralocorticoid or glucocorticoid receptor antagonists.

As will be understood by the skilled artisan, some of the compounds useful for the methods of the present invention may be available for prodrug formulation. As used herein, the term "prodrug" refers to a compound of Formula I which has been structurally modified such that in vivo the prodrug is converted, for example, by hydrolytic, oxidative, reductive, or enzymatic cleavage, into the parent molecule ("drug") as given by Formula I. Such prodrugs may be, for example, metabolically labile ester derivatives of the parent compound where said parent molecule bears a carboxylic acid group. Conventional procedures for the selection and preparation of suitable prodrugs are well known to one of ordinary skill in the art. Conversely, some compounds of the present invention may be suitable as antedrugs. "Antedrugs" are themselves pharmacologically active agents, containing metabolically labile functional groups, that upon administration are subsequently deactivated in vivo. Lee et al., *Arch. Pharm. Res.*, 25(2); 111-136 (2002) provides a discussion of such antedrugs and their utility.

It is also understood that many of the steroid hormone nuclear receptor modulators of the present invention may exist as pharmaceutically acceptable salts and, as such, pharmaceutically acceptable salts are therefore included within the scope of the present invention. The term "pharmaceutically acceptable salt" as used herein, refers to salts of the compounds of Formula I, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of Formula I are capable of forming salts, the pharmaceutically acceptable salts and isoforms thereof are encompassed in the names provided herein.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogen, phosphate, metaphosphate, pyrophosphate, bromide, iodide, hydroiodide, dihydroiodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenyl acetate, phenyl propionate, phenyl butyrate, citrate, lactate, α-hydroxybutyrate, glycolate, tartrate, methanesulfonate, propanesulfonate, naphthalene-1-sulfonate, napththalene-2-sulfonate, mandelate and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of Formula I can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

In addition, as will be appreciated by one of ordinary skill in the art compounds of the present invention containing a carbon-carbon double bond may exist as geometric isomers. Two methods are commonly used to designate the specific isomers, the "cis-trans" method and the "E and Z" method, which methods designate a particular isomer based on whether the groups attached to each of the ethylene carbons are the same or different. A discussion of geometric isomerism and the naming of specific isomers is found in March, "Advanced Organic Chemistry", John Wiley & Sons, 1992, Chapter 4. All such geometric isomers, as well as mixtures of individual isomers, are contemplated and provided by the present invention.

As appreciated by one of ordinary skill in the art, suitable oxygen or nitrogen protecting groups are used as needed. Suitable oxygen or nitrogen protecting groups, as used herein, refers to those groups intended to protect or block the oxygen or nitrogen group against undesirable reactions during synthetic procedures. The suitability of the oxygen or nitrogen protecting group used will depend upon the conditions that will be employed in subsequent reaction steps wherein protection is required, and is well within the knowledge of one of ordinary skill in the art. Commonly used protecting groups suitable for practicing the present invention are disclosed in "Protective Groups in Organic Synthesis, 3$^{rd}$ Edition" by Theodara Greene, Peter G. M. Wuts, John Wiley & Sons, New York (1999).

As used herein the term "($C_1$-$C_4$)alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "($C_1$-$C_6$)alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "($C_1$-$C_4$)alkyl" is included within the definition of "($C_1$-$C_6$)alkyl".

As used herein the term "($C_1$-$C_{10}$)alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like. It is understood that the terms "($C_1$-$C_4$)alkyl" and "($C_1$-$C_6$)alkyl" are included within the definition of "($C_1$-$C_{10}$)alkyl".

As used herein, the terms "Me", "Et", "Pr", "I—Pr", "Bu" and "t-Bu" refer to methyl, ethyl, propyl, isopropyl, butyl and tert-butyl respectively.

As used herein, the term "($C_1$-$C_4$)alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "($C_1$-$C_6$)alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "($C_1$-$C_4$)alkoxy" is included within the definition of "($C_1$-$C_6$)alkoxy".

As used herein, the term "hydroxy($C_1$-$C_4$)alkyl" refers to a straight or branched, monovalent, saturated aliphatic chain of 1 to 4 carbon atoms bearing a hydroxyl group attached to one of the carbon atoms. As used herein, the term "hydroxy($C_1$-$C_6$)alkyl" refers to a straight or branched, monovalent, saturated aliphatic chain of 1 to 6 carbon atoms bearing a hydroxyl group attached to one of the carbon atoms. It is understood that the term "hydroxy($C_1$-$C_4$)alkyl" is included within the definition of "hydroxy($C_1$-$C_6$)alkyl". As used herein, the term "hydroxy($C_1$-$C_4$)alkoxy" refers to an oxygen atom bearing a straight or branched, monovalent, saturated aliphatic chain of 1 to 4 carbon atoms, further bearing a hydroxyl group attached to one of the carbon atoms. As used herein, the term "hydroxy($C_1$-$C_6$)alkoxy" refers to an oxygen atom bearing a straight or branched, monovalent, saturated aliphatic chain of 1 to 6 carbon atoms, further bearing a hydroxyl group attached to one of the carbon atoms. It is understood that the term "hydroxy($C_1$-$C_4$)alkoxy" is included within the definition of "hydroxy($C_1$-$C_6$)alkoxy".

As used herein, the terms "halo", "halide" or "hal" of "Hal" refer to a chlorine, bromine, iodine or fluorine atom, unless otherwise specified herein.

As used herein, the term "halo($C_1$-$C_4$)alkyl" refers to a straight or branched, monovalent, saturated aliphatic chain of 1 to 4 carbon atoms bearing one or more halo groups attached to one or more of the carbon atoms. As used herein, the term "halo($C_1$-$C_6$)alkyl" refers to a straight or branched, monovalent, saturated aliphatic chain of 1 to 6 carbon atoms bearing one or more halo groups attached to one or more of the carbon atoms. It is understood that the term "halo($C_1$-$C_4$)alkyl" is included within the definition of "halo($C_1$-$C_6$)alkyl". As used herein, the term "halo($C_1$-$C_4$)alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo($C_1$-$C_6$)alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo($C_1$-$C_4$)alkoxy" is included within the definition of "halo($C_1$-$C_6$)alkoxy".

As used herein the term "($C_2$-$C_6$)alkenyl" refers to a straight or branched, monovalent, unsaturated aliphatic chain having from two to six carbon atoms and having a double bond. Typical ($C_2$-$C_6$)alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein the term "($C_2$-$C_6$)alkynyl" refers to a straight or branched, monovalent, unsaturated aliphatic chain having from two to six carbon atoms and having a triple bond. Typical ($C_2$-$C_6$)alkynyl groups include propynyl, ethynyl, and the like.

As used herein, the term "acyl" refers to a hydrogen or a ($C_1$-$C_6$)alkyl group attached to a carbonyl group. Typical acyl groups include formyl, acetyl, propionyl, butyryl, valeryl, and caproyl.

As used herein, the term "aryl" refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like As used herein the term "($C_3$-$C_{10}$)cycloalkyl" refers to a saturated hydrocarbon ring structure composed of one or more fused or unfused rings containing from three to ten carbon atoms. Typical ($C_3$-$C_{10}$)cycloalkyl groups include cyclopropyl, cyclobutyl, cyclopentyl, cyclohexyl, cycloheptyl, cyclooctyl, adamantanyl, and the like. "($C_3$-$C_7$)cycloalkyl" refers to a saturated hydrocarbon ring structure composed of one or more fused or unfused rings containing from three to seven carbon atoms. It is understood that the definition of "($C_3$-$C_7$)cycloalkyl" is included within the definition of "($C_3$-$C_{10}$)cycloalkyl".

As used herein, the term "NH—($C_1$-$C_4$) alkylamine" refers to a nitrogen atom substituted with a straight or branched, monovalent, saturated aliphatic chains of 1 to 4 carbon atoms. Included within the term "NH—($C_1$-$C_4$) alkylamine" are —NH($CH_3$), —NH($CH_2CH_3$), —NH($CH_2CH_2CH_3$), —NH($CH_2CH_2CH_2CH_3$), and the like.

As used herein the term "N,N—($C_1$-$C_4$)dialkylamine" refers to a nitrogen atom substituted with two straight or branched, monovalent, saturated aliphatic chains of 1 to 4 carbon atoms. Included within the term "N,N—($C_1$-$C_4$)dialkylamine" are —N($CH_3$)$_2$, —N($CH_2CH_3$)$_2$, —N($CH_2CH_2CH_3$)$_2$, —N($CH_2CH_2CH_2CH_3$)$_2$, —N,N($CH_3$)($CH_2CH_3$), —N,N($CH_2CH_3$)($CH_2CH_3$) and the like.

The designation "▬" refers to a bond that protrudes forward out of the plane of the page.

The designation "⋯⋯⋯I" refers to a bond that protrudes backward out of the plane of the page.

As used herein, the term "steroid hormone nuclear receptor modulator" refers to those nuclear hormone receptor ligands which bind to any one of GR, MR, AR, ER, or PR, of the larger class of nuclear hormone receptors, and either agonize, antagonize, partially agonize, or partially antagonize the receptor's activity.

As used herein the term "mineralocorticoid receptor" or "MR" refers to the mineralocorticoid receptor subtype, of the larger class of nuclear hormone receptors, which binds the mineralocorticoid hormone aldosterone, as its cognate ligand. The term "mineralocorticoid receptor modulator" or "mineralocorticoid modulator" or "MR modulator" as used herein, refers to those nuclear hormone receptor ligands which bind to the mineralocorticoid receptor subtype and modulate (i.e. agonize, antagonize, partially agonize, or partially antagonize) the receptor activity. As a particular embodiment, the present invention provides antagonists of MR activity As used herein the term "glucocorticoid receptor" or "GR" refers to the glucocorticoid receptor subtype, of the larger class of nuclear hormone receptors, which binds the glucocorticoid hormones cortisol, corticosterone, or cortisone as its cognate ligand. The term "glucocorticoid receptor modulator" or "glucocorticoid modulator" or "GR modulator", as used herein, refers to those nuclear hormone receptor ligands which bind to the glucocorticoid receptor subtype and modulate (i.e. agonize, antagonize, partially agonize, or partially antagonize) the receptor activity.

As used herein, the term "disorder susceptible to steroid hormone nuclear receptor modulation" refers to any physiological disorder, of any origin, known or believed to be responsive to administration of a modulator (i.e. agonist, antagonist, partial agonist, or partial antagonist) of a steroid hormone nuclear receptor. Such disorders include Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, esophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cirrhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis, Sweet's disease, type 1 reactive leprosy, capillary hemangiomas, lichen planus, erythema nodosum, acne, hirsutism, toxic epidermal necrolysis, erythema multiform, cutaneous T-cell lymphoma, psychoses, cognitive disorders (such as memory disturbances), mood disorders (such as depression and bipolar disorder), anxiety disorders, and personality disorders.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances:

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

Oral administration is a preferred route of administering the compounds employed in the present invention whether administered alone, or as a combination of compounds capable of acting as a steroid hormone nuclear receptor modulator. Oral administration, however, is not the only route, nor even the only preferred route. Other preferred routes of administration include transdermal, percutaneous, pulmonary, intravenous, intramuscular, intranasal, buccal, sublingual, or intrarectal routes. Where the steroid hormone nuclear receptor modulator is administered as a combination of compounds, one of the compounds may be administered by one route, such as oral, and the other may be administered by the transdermal, percutaneous, pulmonary, intravenous, intramuscular, intranasal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of Formula I are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, as described herein and above, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently; Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating physiological disorders susceptible to steroid hormone nuclear receptor modulation, and particularly congestive heart failure.

Particular Aspects of the Compounds and Methods of the Invention

The following list sets out several groupings of particular substituents for compounds of Formula I. It will be understood that compounds of Formula I having such particular substituents, and the methods employing such compounds, represent particular aspects of the present invention. It will be further understood that each of these groupings of particular substituents may be combined with other provided groupings, to create still additional particular aspects of the compounds of the present invention Therefore, a particular aspect of the present invention is one wherein the compound of Formula I, is one wherein:
(a) Y represents CH2; or
(b) Y represents O;
(c) $R^1$ represents hydrogen;
(d) $R^1$ represents fluoro;
(e) $R^2$ represents hydrogen; or
(f) $R^2$ represents fluoro;
(g) $R^3$ represents a group of the formula:

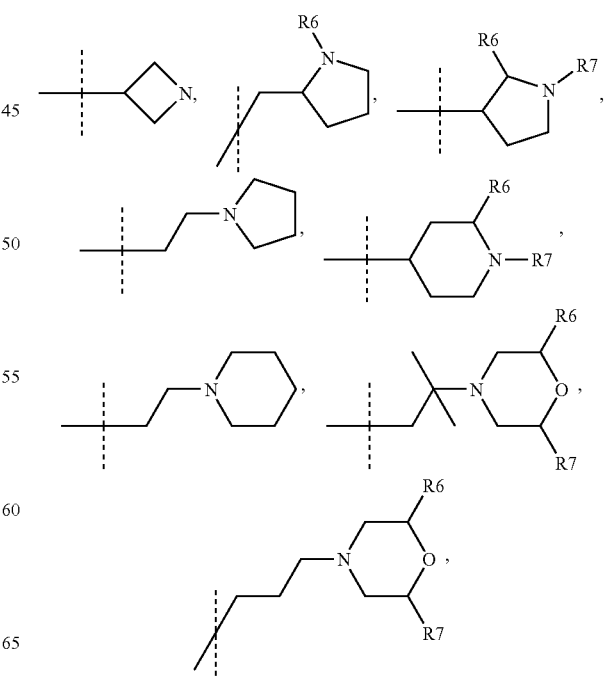

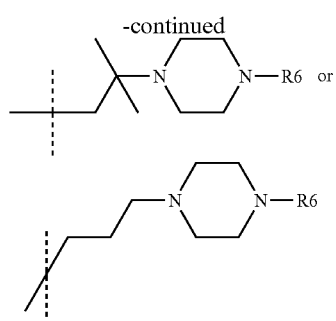
(f) R3 represents a group of the formula
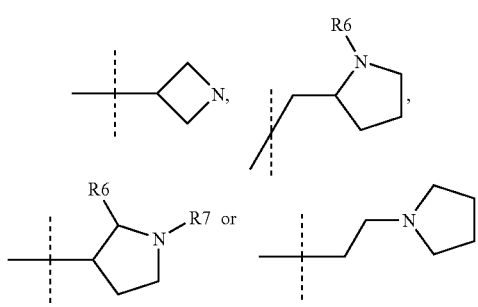
(g) R3 represents a group of the formula
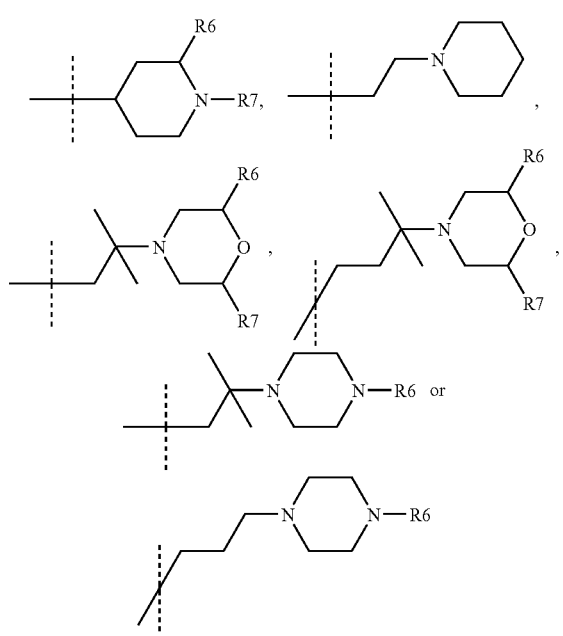
(h) R3 represents a group of the formula
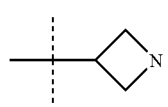
(i) R3 represents a group of the formula
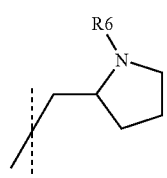
(j) R3 represents a group of the formula
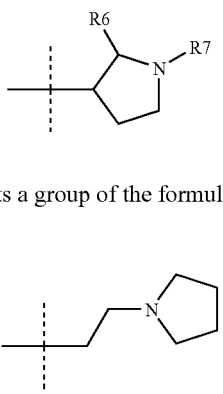
(k) R3 represents a group of the formula
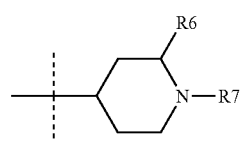
(l) R3 represents a group of the formula
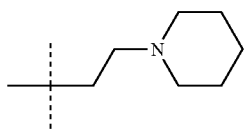
(m) R3 represents a group of the formula
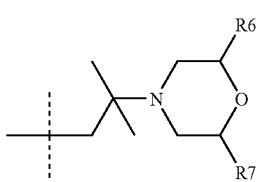
(n) R3 represents a group of the formula (o) R3 represents a group of the formula

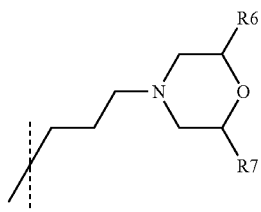

(p) R3 represents a group of the formula

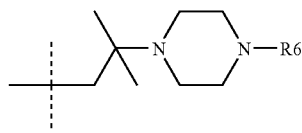

(q) R3 represents a group of the formula

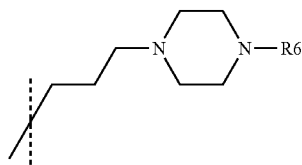

In addition, it will be understood that a most particular aspect of the present invention is provided by each of the individual compounds exemplified herein.

Compounds of Formula I can be chemically prepared, for example, by following the synthetic routes set forth in the Schemes below. However, the following discussion is not intended to be limiting to the scope of the present invention in any way. For example, the specific synthetic steps for the routes described herein may be combined in different ways, or with steps from different schemes, to prepare additional compounds of Formula I. Further, it should be recognized that the sequence in which the synthetic reactions take place is not implied and can be done in any fashion to achieve the desired final product.

All substituents, unless otherwise indicated, are as previously defined. The reagents and starting materials are readily available to one of ordinary skill in the art. For example, certain reagents or starting materials can be prepared by one of ordinary skill in the art following procedures disclosed in All substituents, unless otherwise indicated, are as previously defined. The reagents and starting materials are readily available to one of ordinary skill in the art. For example, certain reagents or starting materials can be prepared by one of ordinary skill in the art following procedures disclosed in J. Prakt. Chem. 333 (4) (1991); J. Marsh, Advanced Organic Chemistry (4$^{th}$ edition); J. Med. Chem. (1990); J. S. Buck and W. S. Ide, Organic Synthesis Coll. Vol. II, 622-623, (1943) J. P. Wolfe and S. L. Buchwald, Organic Synthesis, (78) 23-31 (2000); Tetrahedron Letters, 39 (51) 9365-9368 (1998); F. Kurzer, Organic Synthesis, Coll. Vol. (IV) 49 (1963); and Synthetic Communications, 1129-1135 (1991). Additional reagents, starting materials, or useful procedures may be found in M Kurokawa, F Sato, Y Masuda, T Yoshida and Y Ochi, Chem. Pharm. Bull., 39; 10; (1991) 2564-5273, Y Ohishi, H Yoshitaka, M Mitsuo, T Mukai, K Kimura, M Nagahara, Chem. Pharm. Bull., 38; 4; (1990) 1066-1068, Inman, Raiford, JACS; 56 (1934) 1586-1587, Clark, Pessolano, JACS; 80 (1958) 1662, P. Bollinger, P. Cooper.; H. U. Gubler, A. Leutwiler, T. Payne Helv. Chem. Acta; 73; (1990); 197, G. Vassilikogiannakis, M. Hatzimarinaki, M. Orfanapoulos J. Org. Chem., 65, 8180; Y. Girard, J. G. Atkinson, P. C. Belanger, J. J. Fuentes, J. Rokach, C. S. Rooney, D. C. Remy, C. A. Hunt J. Org. Chem., 48; (1983); 3220, D. S. Matteson, D. Majumder Organometallics, 2; (1983); 230; Journal of Heterocyclic Chemistry, 73; (1971) Journal of Medicinal Chemistry, 33; (1990); 3095, Journal of Organic Chemistry, 60; (1995); 7508, Bergmann, E. D., Solomonovici, A., Synthesis, (1970); 183-189, Poirier et al., Org. Letters, 3; 23; (2001); 3795-3798, Spanish Patent ES2092957 A1(1996); Brown, C., et al., J. Chem. Soc., Perkin Trans. I, 3007 (1982); Deck, L. M., et al., Org. Prep. Proceed. Int., 22(4); 495-500, (1990); Lee, J. C., et al., Synth. Comm., 25(9), 1367-1370 (1995); Ho, Z. C., et al., Tetrahedron, 52(41), 13189-13200 (1996); M Murata, T Takashi, S Watanabe and Y Yusuru, J. Org. Chem.; 65 (1) 164-168 (2000); and T. Ishiyama, M. Murata, N. Miyaura, J. Org. Chem., 60(23), 7508-7510 (1995); A. R. Ramesha and A. K. Roy, Syn. Comm. 31 (16) 2419-2422 (2001); F. J. Villani et al., J. Heterocycl. Chem. (8) 73-81 (1971), F. J. Villani et al, J. Med. Chem. 15 (7) 750-754 (1972); M. Noda, Chem. Pharm. Bull. 46 (7) 1157-1159 (1998); K. Inoue et al, Synthesis, (1) 113-116 (1997); and W. S. Trahanovsky et al, J. Organic Chem., 60 (26) 8407-8409 (1995). Other necessary reagents and starting material may be made by procedures which are selected from standard techniques of organic and heterocyclic chemistry, techniques which are analogous to the syntheses of known structurally similar compounds, and the procedures described in the Examples below, including any novel procedures. In addition, one of ordinary skill in the art will readily appreciate that many of the necessary reagents and starting materials are available from commercial suppliers.

Schemes I and II provide procedures useful for the synthesis of boronic acid ester intermediates useful for the synthesis of compounds of Formula I.

Scheme I

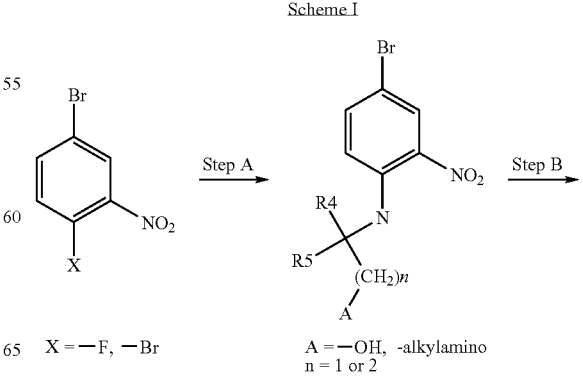

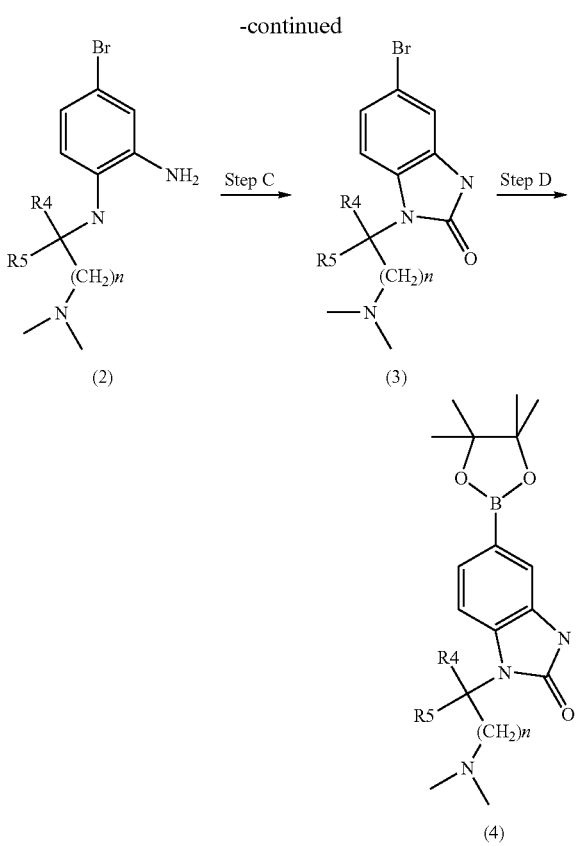

In Scheme I, Step D, under a blanket of nitrogen, a solution of the compound of structure (3) in THF is cooled to about 5° C. and 3N ethylmagnesium bromide is added. After about ½ h, the reaction is cooled to about −72° C. and slowly 1.7M t-BuLi is added. The reaction is allowed to warm to about −55° C., then trimethyl borate is added and the reaction is allowed to stir at room temperature overnight. 5N HCl is then added and the reaction stirred for about 4 h. The pH is adjusted to about 6-7 and the crude boronic acid is extracted into ethyl acetate, dried and concentrated to give the crude acid which is then slurried with toluene and pinacol is added. The reaction is heated briefly and stirred overnight. Ethyl acetate and aqueous NaHCO3 are added, the organics extracted with water and the dried (MgSO4) organic layer is evaporated to give the purified product of compound (4). Alternatively, the compound of structure (3) can be mixed with 1.1 eq pinacol diborane, 0.14 eq tricyclohexylphosphine, 3 eq KOAc in DMSO. The reaction is sparged with nitrogen for 10 min and then 0.06 eq tris(dibenzylideneacetone)dipalladium (0) is added and the reaction heated at 80-110° C. for 4-24 h under a blanket of nitrogen. The cooled reaction is partitioned between water and ethyl acetate. The organic layer is washed a second time with water, dried and concentrated to give the crude pinacol ester of structure (4). The product of structure (4) may be purified or used without further purification.

In Scheme I, Step A where A=alkylamino, an appropriately substituted nitrobenzene derivative such as 5-bromo-2-fluoro-nitrobenzene or other 2,5-dihalonitrobenzene is mixed with about 2-10 equivalents of a substituted amine with or without an inert solvent such as THF or dioxane. The reaction is stirred at room temperature to 100° C. for about 1-18 h. The solvent is removed under reduced pressure and the residue partitioned between water and ethyl acetate. The organic layer is dried (MgSO4) and concentrated to provide compound of structure (1).

In Scheme I, Step B, the compound of structure (1) is dissolved in ethyl acetate or THF and 5% Pt/C (sulfided) is added. The slurry is placed under 60 psi hydrogen gas at room temperature for about 8 h. The reaction is then filtered and concentrated to provide the compound of structure (2). Compound (2) may then be purified, for example by using a short plug of silica gel and 10% 3N NH3 in MeOH/dichloromethane.

In Scheme I, Step C, the compound of structure (2) is mixed with NaHCO3, water, and methanol. Slowly, phenyl chloroformate (about 1.5 equivalents) is added and the reaction is stirred for about 1 h at room temperature. 5N NaOH (about 1.5 equivalents) is then added and the reaction is stirred overnight at room temperature. The solid of structure (3) is collected by vacuum filtration and washed with methanol. Alternatively, structure (2) can be dissolved in THF or dioxane that contains 3-10 eq triethylamine and cooled to 0° C. Solid triphosgene is added slowly (exothermic) and then the reaction is stirred at room temperature for 4-24 h. The reaction is poured into an excess of water and basified with dilute NaOH. The product is extracted into ethyl acetate and then purified by column chromatography using methylene chloride containing 3N ammonia in MeOH.

Scheme II

Structure (1) (A = —OH) — Step A →

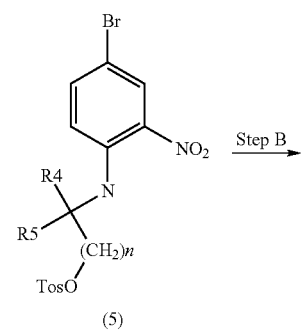

(5) — Step B →

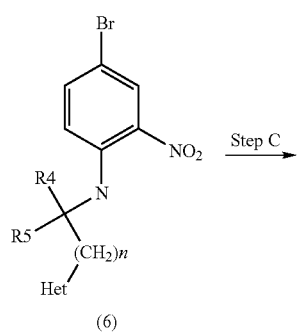

(6) — Step C →

-continued

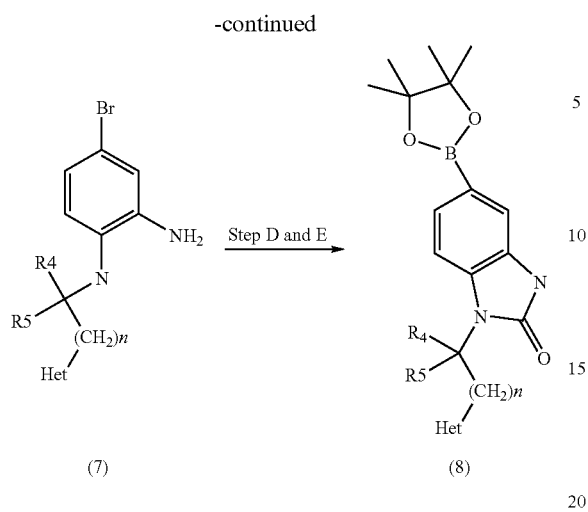

In Scheme II, Step A, the compound of structure (1) where A represents a hydroxy group (prepared as described in Scheme I above) is reacted with tosyl anhydride in an inert solvent such as chloroform, carbon tetrachloride or methylene chloride containing 3-5 eq of pyridine and 0.1-0.5 eq DMAP to provide the tosylate intermediate of structure (5).

In Scheme II, Step B the intermediate tosylate of structure (5) is converted to intermediates of structure (6) by mixing with a substituted or unsubstituted amine heterocycle, with or without solvent, and heating at 30-100° C. for 2-18 h.

In Scheme II, Step C, the intermediate of structure (6) is dissolved in ethyl acetate or THF and 5% Pt/C (sulfided) is added. The slurry is placed under 60 psi hydrogen gas at room temperature for about 8 h. The reaction is then filtered and concentrated to provide the compound of structure (7). Compound (7) may then be purified, for example by using a short plug of silica gel and 10% 3N NH3 in MeOH/dichloromethane.

In Scheme II, Steps D and E, the compound of structure (7) is reacted in a sequence of steps as described in Scheme I, Steps C and D above to provide the borate intermediate of structure (8).

Scheme III provides procedures for the synthesis of compounds of Formula I from a tricyclic vinyl bromide and an aryl boronic acid derivative (prepared, for example, as described in Schemes I and II above).

Scheme III

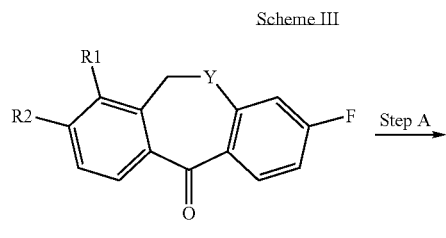

Y represents CH2 or O

-continued

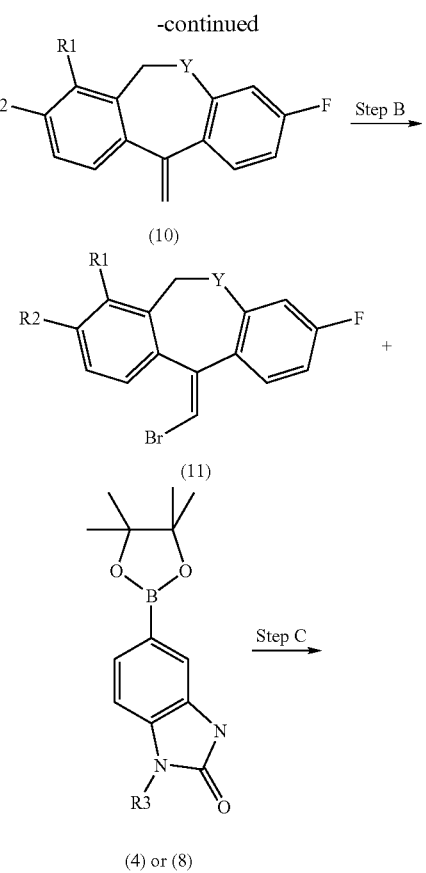

(4) or (8)

R3 is as defined in Formula I

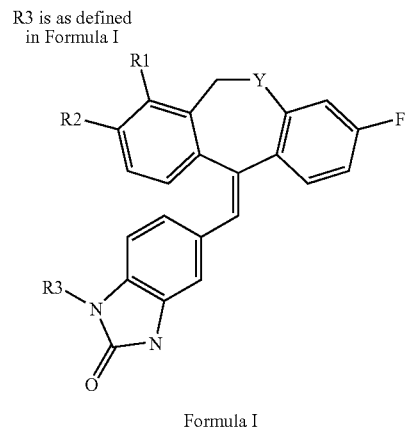

Formula I

In Scheme III, Step A, the dibenzooxepine or dibenzosuberone derivative (9) is dissolved in an appropriate solvent such as diethyl ether, dioxane or tetrahydrofuran and 1 to 5 equivalents of methylmagnesium bromide is added. After 2-24 hours, the intermediate carbinol derivative is converted to the exomethylene derivative by cooling to 0° C. and adding HCl. After stirring for about 1-18 hours, the reaction is shaken with EtOAc and water. The organic solution is dried (MgSO4) and concentrated. The crude product of structure (10) is purified by short path column chromatography (silica gel, hexane containing EtOAc).

In Step B, the compound of structure (10) is dissolved in a solvent such as methylene chloride, chloroform, carbon tetrachloride or 1,2-dichloroethane and treated with a slight excess of 4-(dimethylamino)pyridinium tribromide. The reaction is stirred at room temperature for about 1-24 hours. The excess brominating reagent is quenched with $Na_2SO_3$ and the reaction is partitioned between water and organic solvent. The solvent is dried ($Na_2SO_4$) and concentrated under reduced pressure to yield the crude product of structure (11). The crude compound of structure (11) is purified by short path column chromatography (silica gel, hexane containing EtOAc). As will be appreciated by one of ordinary skill in the art, each of the geometric isomers of structure (11) can be selectively separated using standard techniques such as recrystallization with an appropriate solvent such as MeOH.

In Step C, the vinyl bromide of structure (11) and aryl boronic acid derivative ((4) or (8)) are mixed in dioxane. 2.0M aqueous $Na_2CO_3$ is then added and the reaction sparged with $N_2$ for 5 min. $Pd(PPh_3)_4$ is added and the reaction vial immediately sealed. The reaction is heated to about t 70-100° C. for about 8-24 h. The reaction is then quenched with $H_2O$ and the product of Formula I extracted into $CH_2Cl_2$. After drying ($Na_2SO_4$) and concentration, the crude product is purified using chromatography on silica gel, eluting with ethyl acetate/hexanes to obtain the purified product of Formula I.

Scheme IV provides procedures for the synthesis of compounds of Formula I wherein R3 represents an alkyl substituted heterocyclic alkyl moiety.

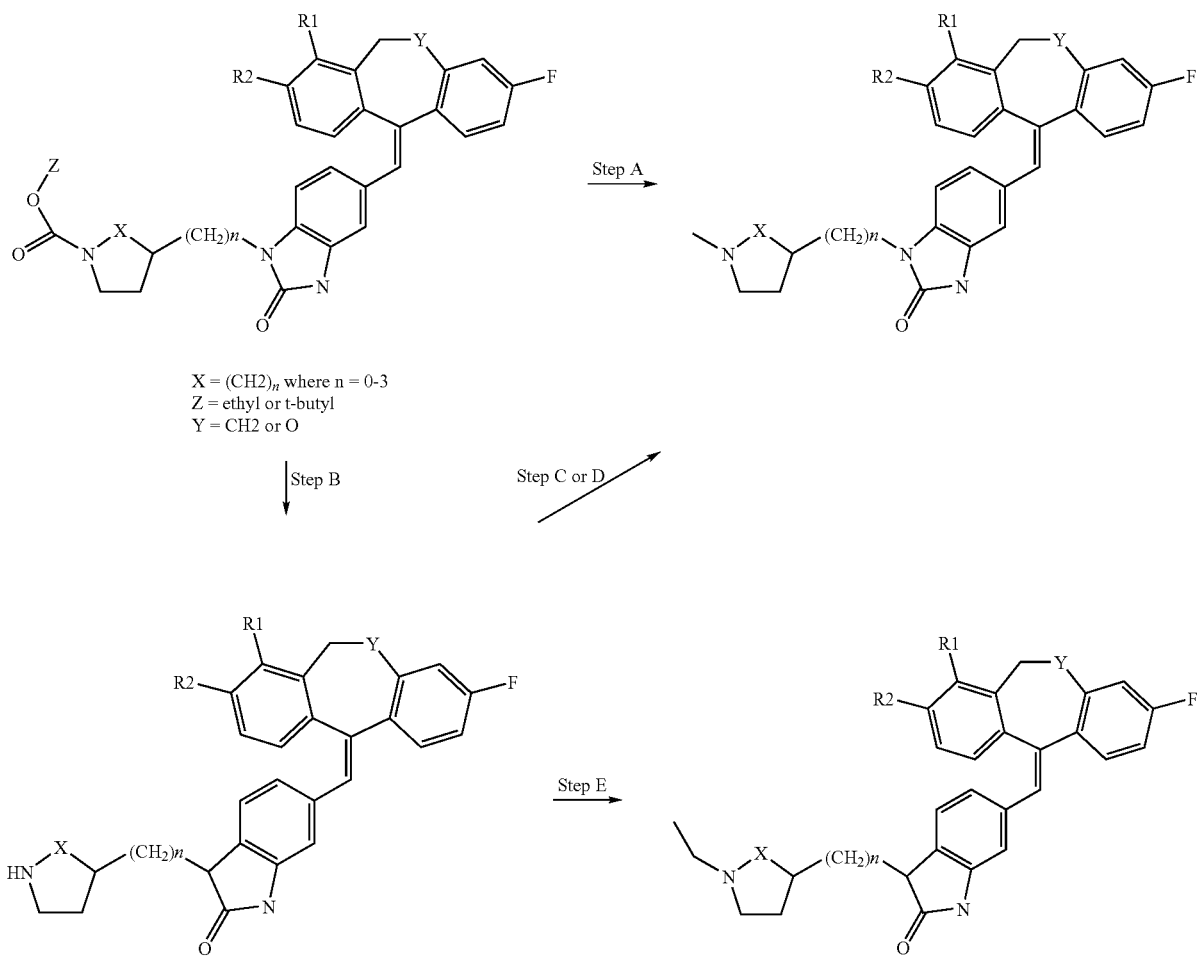

Step (a) LAH/THF;
Step (b) 4M HCl in dioxane;
Step (c) 40% aqueous formaldehyde, NaBH(OAc)₃, DCE;
Step (d) 40% aqueous formaldehyde/HCOOH, heat;
Step (e) acetaldehyde, NaBH(OAc)3, DCE Scheme IV provides well known procedures for the preparation of N-methyl and N-ethyl derivatives of Formula I from N-protected Formula I precursors. For example, the use of LAH to reduce a BOC group to a methyl as shown in Step A of Scheme IV is similar to that reported by J Cossy et al, *JOC* 67; 1982-1992 (2002) and F Acquadro et al, *Tetra. Lett.* 43; 8759-8763 (2002). The reductive animation in Scheme IV, Steps C and E follows a similar procedure to that reported by AF Abdel-Magid et al, *JOC* 61; 3849-3862 (1996). Finally, the use of formaldehyde/formic acid to methylate as in Step D, is reported by A M McLeod et al, *J Med Chem* 33; 2052-2059 (1990).

Schemes V(a), V(b), and VI provide alternative general procedures that may be useful in the preparation of compounds of Formula I.

In Scheme V(a), Step A, the compound of structure (11) is coupled with the aryl boronic acid derivative of structure (12) according to procedures essentially as described previously in Scheme III, Step C above, to provide the compound of structure (13). Alternatively, in Step B, the compound of structure (11) is coupled with the boronic acid derivative of

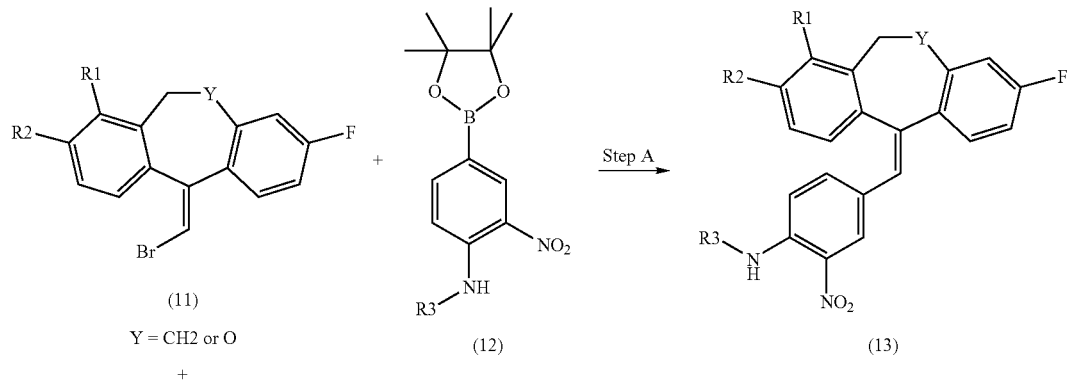

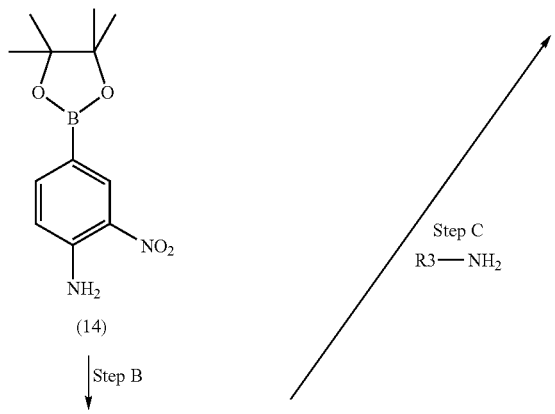

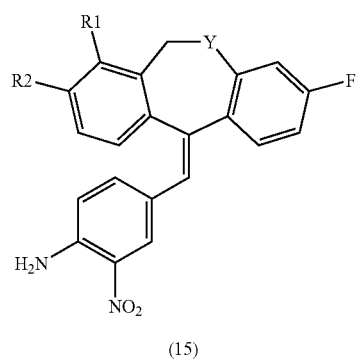

structure (14) (unsubstituted amine) according to the procedures as described in Scheme III, Step C to provide the compound of structure (15).

In Scheme V(a), Step C, the compound of structure (15) can be readily converted to the compound of structure (13) utilizing known amine functionalization techniques such as alkylation, reductive alkylation, acetylation, and the like.

about 18 h. On completion of the hydrogenation, the reaction slurry is filtered through a Hyflo pad and triethyl amine is added. The solution is cooled to about 0 degrees Celsius, and a THF solution of triphosgene is added. On completion of the reaction, the reaction mixture is filtered (to remove insoluble triethylamine chloride) and the solvent is removed in vacuo to yield the crude product of Formula I. The final product may

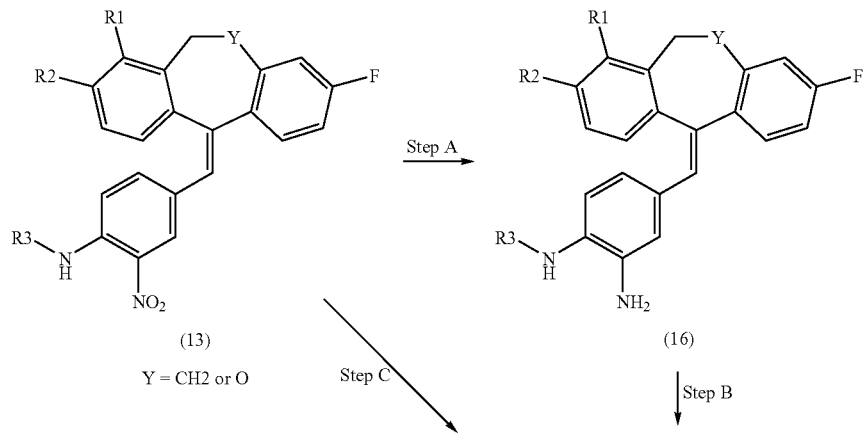

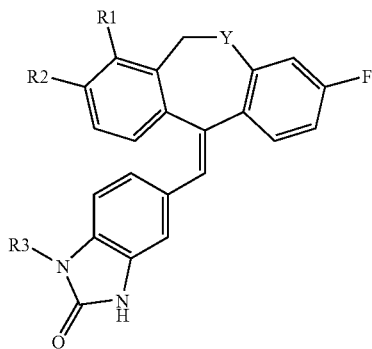

Formula I

In Scheme V(b), Step A, the compound of structure (13) is treated according to procedures essentially as described in Scheme I, Step B above, to provide the compound of structure (16). In Step B, the compound of structure (16) is combined with triethylamine (about 3 eq) in a suitable solvent such as dichloromethane. With stirring, triphosgene is slowly added and the reaction stirred for about 15 min. The reaction mixture is then diluted with tetrahydrofuran and dichloromethane then washed with brine, water and brine. The organic layer is then dried (MgSO4) and concentrated to provide the crude product of Formula I. The crude product may then be purified by standard techniques such as flash chromatography.

Alternatively, in Step C, the compound of structure (13) is dissolved in a suitable solvent such as THF in the presence of 5% platinum on carbon. The reaction mixture is hydrogenated at a pressure of 50 psi Hydrogen on a Parr shaker for then be purified by standard techniques such as repeated reslurries from an appropriate solvent such as methanol.

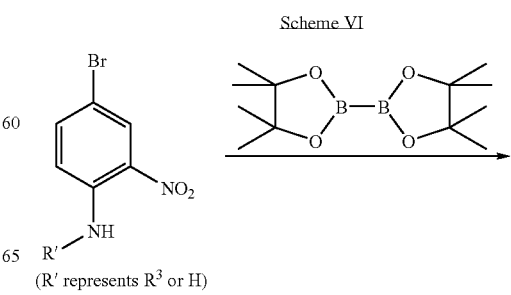

($R'$ represents $R^3$ or H)

-continued

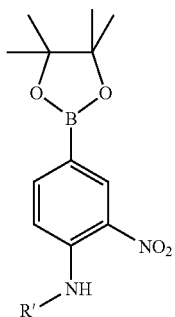

(12) (R' represents R3)
(14) (R' represents H)

In Scheme VI, 5-bromo-2-amino nitrobenzene or 5-bromo-2alkylamino nitrobenzene (made for example from 5-nitro-2-fluoro nitrobenzene mixed with about 2 eq. of an appropriately substituted amine in a suitable solvent such as THF, and stirred at room temperature for about 18 hours) is reacted with bis(pinacoloto)diboron, according to the method of N. Miyaura et al., *JOC* 60; 7508-7510 (1995), to provide a product of structures (12) or (14).

Where is it desired to make compounds of Formula I in a stereo-selective manner, general procedures essentially as provided in Schemes VII(a) and (b) may be useful to prepare intermediates. The final products of each of these schemes can then be readily converted into compounds of Formula I by one of skill in the art In Scheme VII(a), Step A a palladium catalyst (such as PdCl$_2$(dppf)CH$_2$Cl$_2$), an alkyne of structure (1), an alkyl boronic acid derivative, and a suitable base (such as Cs$_2$CO$_3$) are combined in a suitable organic solvent such as THF or DME. The reaction mixture is heated under nitrogen at 80 to 110 degree overnight. The solvent is evaporated and the residue may then be loaded on silica gel column and eluted with organic solvent (EtOAc/hexane) to provide the compound of structure (II).

Alternatively, in Step B, a mixture of the alkyne of structure (I), a palladium catalyst (such as Pd(Oac)$_2$) and an appropriate ligand such as tri-O-tolylphosphine are dissolved in a suitable solvent such as acetonitrile, and stirred under nitrogen at room temperature. Formic acid is then added dropwise followed by a suitable base such as piperidine. The reaction mixture is heated at about 80° C. for about 4-24 h. The reaction mixture is then concentrated to a residue by standard techniques and may then be purified through silica gel to give cyclized product of structure (III).

Scheme VII(a)

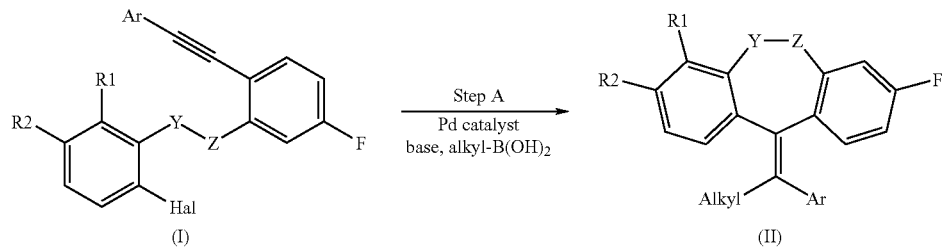

(Ar is unsubstituted or substituted aryl or benzofused heterocycle)

(Y—Z is CH2—O, O—CH2, or CH2—CH2)

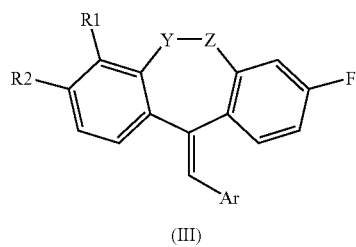

Scheme VII(b)

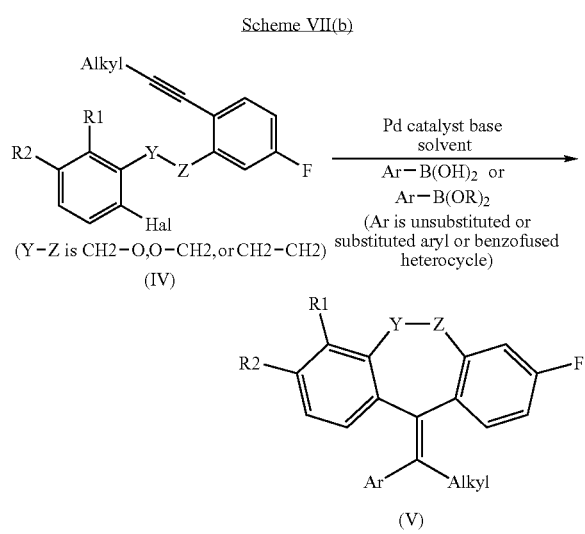

In Scheme VII(b), an alkyne of structure (IV), an aryl boronic acid derivative such as 3-nitrophenyl boronic acid, a palladium catalyst (such as Pd(Oac)$_2$) and a suitable base such as Na$_2$CO$_3$ are combined and the reaction flask flushed with nitrogen. A suitable solvent such as dioxane/water is added to the mixture and the reaction is heated under nitrogen at about 80 degrees Celsius overnight. The reaction mixture is diluted with EtOAc and water and the layers separated. The aqueous layer is again extracted with EtOAc. The combined organic layers are dried, concentrated by standard techniques, and the residue purified by standard methods such as column chromatography to provide the compound of structure (V)

Starting materials useful for practicing the procedures describe in Schemes VII (a) and (b) may be readily prepared by one of skill in the art using known methods. For example Tykwinski, R. R., *Angew Chem. Int. Ed.*, 42, 1566 (2003); Rossi, R., Carpita, A., and Belina, F. *Org. Prep. Proc. Int.* 27, 129 (1995); Campbell, I. B., *Organocopper Reagents*, 217. Ed.: Taylor, R. J. K. Publisher: IRL Press, Oxford, UK (1994); and Sonogashira, K., Tohda, Y., and Hagihara, N., *Tetrahedron Lett.* 4467 (1975) provide general procedures for the synthesis of the alkynes. Furthermore, biaryl ether substrates for use in Schemes VII (a) and (b) may be prepared according to the general procedures described in Hughes, David L., *Organic Reactions* (New York) 42, 335-656 (1992); and Mitsunobu, O., *Synthesis* 1, (1981).

Determination of Biological Activity:

To demonstrate that compounds of the present invention have affinity for steroid hormone nuclear receptors, and thus have the capacity to modulate steroid hormone nuclear receptors, soluble MR and GR binding assays are performed. All ligands, radioligands, solvents, and reagents employed in the binding assays are readily available from commercial sources, or can be readily synthesized by the ordinarily skilled artisan.

Mineralocorticoid Receptor Binding Assay (Method 1):

The full length human MR gene is cloned from a human kidney or human brain cDNA library. Briefly, using synthetic oligonucleotide primers (Eli Lilly and Company, Indianapolis) directed to nucleotides 20-54 and 3700-3666 of the human MR, polymerase chain reaction (PCR) is performed under standard conditions using a human cDNA library. The PCR reaction is performed in a final volume of 50 µl containing about 1 µl of a 50× stock solution of polymerase; about 1 µl of a 50× stock solution of dNTP; about 5 µl of an appropriate PCR buffer; about 1 µl of each primer; about 5 µl of a H. kidney or H. brain cDNA library; and about 36 µl of water. The reaction is allowed to denature for about 30 seconds at 95 degrees Celsius, anneal for about 30 seconds at 55 degrees Celsius, and extend for about 5 minutes at 72 degrees Celsius, the sequence being repeated for a total of about 35 cycles. The desired PCR product (3.68 Kb) is confirmed by gel electrophoresis and subsequently cut from the gel and stored at about −20 degrees Celsius until extraction. To extract the cDNA product from the agarose gel, the QIAEX II Gel Extraction protocol (QIAGEN, Inc.) is employed according to the manufacturer's instructions. Following extraction, the MR cDNA is cloned into an appropriate cloning vector (Zero Blunt TOPO PCR Cloning Kit (Invitrogen, Inc.) and a pAcHLT-baculovirus transfer vector (B.D./Pharminogen), then expressed in SF9 insect cells, essentially according to manufacturer's instructions. Sf9 cells are grown at a scale where gram quantity cell pellets are obtained for subsequent use in the MR binding assay. Harvested cell pellets are lysed by repeated freeze-thaw cycles (about 4) in a suitable lysis buffer then centrifuged at about 1×10$^3$ G (with the supernatant being saved for future assays).

MR binding assays are performed in a final total volume of about 250 µl containing about 20-25 µg of protein and 0.5 nM of [$^3$H]-aldosterone plus varying concentrations of test compound or vehicle. The assay binding buffer consists of 30 mM sodium molybdate, 30 mM of TRIS-HCl, 5 mM sodium phosphate, 5 mM sodium pyrophosphate, and about 10% glycerol, pH=7.5.

Briefly, assays are prepared at RT in 96-well Falcon 3072 plates, each well containing 210 µl of binding buffer, 10 µl of [$^3$H]-aldosterone, 10 µl of test compound/vehicle, and 20 µl of the resuspended receptor protein extract. Incubations are carried out at 4 degrees Celsius with shaking for about 16 hours. 200 µl aliquots of each incubation are filtered onto Millipore HA 0.45 micron 96-well filter plates, pre-moistened with cold 30 mM TRIS-HCl. The filter plates are suctioned dry with vacuum and immediately washed 3× with cold 30 mM TRIS-HCl. The plates are then punched out and the amount of receptor-ligand complex is determined by liquid scintillation counting using 4 ml of Ready Protein Plus™ liquid scintillation cocktail.

IC$_{50}$ values (defined as the concentration of test compound required to decrease [$^3$H]-aldosterone binding by 50%) are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition (IC$_{50}$) of an Enzymatic Reaction, Biochem. Pharmacol., 22: 3099-31088; (1973).

Glucocorticoid Receptor Binding Assay (Method 1):

To demonstrate the GR modulating potency of compounds of the present invention the following source of glucocorticoid receptor is employed. A549 human lung epithelial cells (ATCC) are grown at a scale where gram quantity cell pellets are obtained. Harvested cell pellets are washed twice in cold phosphate buffered saline, centrifuged, and resuspended in cold assay binding buffer. The assay binding buffer consists of 10% glycerol, 50 mM Tris-HCl (pH7.2), 75 mM sodium chloride, 1.5 mM magnesium chloride, 1.5 mM EDTA, and 10 mM sodium molybdate. Cell suspensions were lysed via sonication, centrifuged, and the "extract" supernatant is snap frozen and stored at −80 C until needed.

GR binding assays are performed in a final volume of 140 ul containing 50-200 ug of A549 cell extract and 1.86 nM [$^3$H]-dexamethasone (Amersham) plus varying concentrations of test compound or vehicle. Briefly, assays are prepared at RT in 96-well Fisher 3356 plates, each well containing 100 ul of A549 cell extract, 20 ul of [$^3$H]-dexamethasone, and 20 ul of test compound/vehicle. Incubations are carried out at 4 degrees Celsius for 16 hours. After incubation, 70 ul of 3× dextran-coated charcoal solution is added to each reaction, mixed, and incubated for 8 minutes at RT. 3×-dextran-coated charcoal solution consists of 250 ml assay binding buffer, 3.75 g Norit A charcoal (Sigma), and 1.25 g dextran T-70 (Amersham). Charcoal/unbound radioligand complexes are removed by centrifugation of the plate and 140 ul of supernatant from each well is transferred to another 96 well Optiplate (Packard Instruments). 200 ul of Microscint-20 scinillant (Packard Instruments) is added to each well and amount of receptor bound radioligand is determined using Packard Instruments TopCount instrument.

$IC_{50}$ values, defined as the concentration of test compound required to decrease [$^3$H]-dexamethasone binding by 50%, are then determined. Ki values for each respective test compound can then be calculated by application of the Cheng-Prusoff equation as described in Cheng et al., Relationship Between The Inhibition Constant (Ki) and The Concentration of Inhibitor Which Causes 50% Inhibition ($IC_{50}$) of an Enzymatic Reaction, Biochem. Pharmacol., 22: 3099-31088; (1973).

Alternative Binding Assay Protocol for MR, GR, AR, and PR (Method 2):

Cell lysates from 293 cells overexpressing human GR (glucocorticoid receptor), AR (androgen receptor), MR (mineralocorticoid receptor) or PR (progesterone receptor) are used for competition binding assays to determine Ki values for test compounds. Briefly, competition binding assays are run in a buffer containing 20 mM Hepes, pH 7.6, 0.2 mM EDTA, 75 mM NaCl, 1.5 mM MgCl2, 20% glycerol, 20 mM sodium molybdate, 0.2 mM DTT, 20 ug/ml aprotinin and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added at various concentrations in half-log increments. Non-specific binding is determined in the presence of 500 nM dexamethasone for GR binding, 500 nM aldosterone for MR binding, or 500 nM methyltrienolone for AR and PR binding. The binding reaction (140 μl) is incubated for overnight at 4° C., then 70 μl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 μl of the mix is transferred to another 96-well plate and 175 μl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an $IC_{50}$ and % Inhibition at 10 μM. The $K_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The $IC_{50}$ values for compounds are converted to $K_i$ using Cheng-Prusoff equation and the $K_d$ determined by saturation binding assay.

Binding assay protocols for steroid hormone nuclear receptors similar to those described above can be readily designed by the ordinarily skilled artisan. U.S. Pat. No. 6,166,013 provides examples of such protocols. Representative compounds of the present invention have a Ki in the MR or GR binding assay of ≦50 μM. Table I (see below) provides MR and GR binding data for a representative sample of the exemplified compounds of the present invention.

To demonstrate the ability of compounds of the present invention to modulate the activity of a steroid hormone nuclear receptor (i.e. either agonize, antagonize, partially agonize, or partially antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Mineralocorticoid Receptor Modulation (Method 1):

For the MR transient transfection assay, COS-7 cells are transfected with full length human MR and a 2XGRE-luciferase gene construct. Following transfection, the ability of test compounds to modulate expression of the luciferase reporter gene product is monitored. Briefly, on day one, COS cells are harvested from cell culture plates using standard procedures such as treatment with Trypsin-EDTA (GIBCO BRL). Culture medium is then added to the cells and the cell-medium mixture is plated in 96-well plates coated with poly-(d)-lysine (approximately $3 \times 10^4$ cells/well). Cells are grown for about 4 hours then transfected with Fugene-6 reagent with plasmids containing human MR, previously cloned into pc.DNA 3.1 expression vector, and 2XGRE-reporter gene construct (GRE-luciferase), previously cloned into pTAL-luc vector. Transfection is carried out in DMEM with 5% fetal calf serum, charcoal treated. 24 hours later cells are exposed to various concentrations of aldosterone in the presence and absence of test compound and incubated for an additional 24 hours. The reaction is terminated by the addition of lysis buffer followed by luciferin (luciferase substrate). Luciferase expression, as an indicator of ligand induced MR transactivation, is monitored by chemiluminescence measured using a microtiter plate luminometer (MLX). The kinetic inhibition constant ($K_b$ or $K_p$) can then be determined by analysis of dose-response curves for aldosterone, in the presence and absence of test compound, using standard techniques.

Alternative Functional Assay for MR, GR, PR, and AR Activity (Method 2):

Human embryonic kidney hEK293 cells are co-transfected using Fugene. Briefly, the reporter plasmid containing two copies of GRE (glucocorticoid response element $^5$'TGTA-CAGGATGTTCT$^3$') (SEQ ID NO:1) and TK promoter upstream of the luciferase reporter cDNA, is transfected with a plasmid constitutively expressing either human glucocorticoid receptor (GR), human mineralocorticoid receptor (MR), or human progesterone receptor (PR), using viral CMV promoter. The reporter plasmid containing two copies of probasin ARE (androgen response element $^5$'GGTTCTTGGAG-TACT$^3$') (SEQ ID NO:2) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 5% charcoal-stripped Fetal Bovine Serum (FBS). After a overnight incubation, transfected cells are trypsinized, plated in 96 well dishes in DMEM media containing 5% charcoal-stripped FBS, incubated for 4 h and then exposed various concentrations of test compounds in half log increments. In the antagonist assays low concentrations of agonist for each respective receptor are added to the media (0.25 nM dexamethosone for GR, 0.3 nM of methyltrienolone for AR, 0.05 nM of progesterone for PR and 0.05 nM aldosterone). After 24 h of incubations with compounds, cells are lysed and luciferase activity is determined. Data is fit to a 4 parameter-fit logistics to determine EC50 values. The % efficacy is determined versus maximum stimulation obtained with 100 nM methyltrienolone for AR assay, with 30 nM progesterone for PR assay, with 30 nM aldosterone for MR assay and with 100 nM dexametasone for GR assay.

TABLE I

Mineralocorticoid and Glucocorticoid Receptor Binding Assay Values

| Example No. | MR Ki (nM) Method 1 | GR Ki (nM) Method 1 | GR Ki (nM) Method 2 |
|---|---|---|---|
| 1 | +++ | -- | ++ |
| 2 | +++ | -- | ++ |
| 3 | +++ | -- | +++ |
| 4 | +++ | -- | ++ |
| 5 | +++ | -- | +++ |
| 6 | +++ | + | -- |
| 7 | +++ | -- | +++ |
| 8 | +++ | -- | +++ |
| 9 | +++ | -- | +++ |
| 10 | +++ | -- | +++ |
| 11 | +++ | -- | +++ |
| 12 | +++ | -- | ++ |
| 13 | +++ | -- | +++ |
| 14 | +++ | -- | +++ |
| 15 | +++ | -- | +++ |
| 16 | +++ | -- | +++ |
| 17 | +++ | -- | +++ |
| 18 | +++ | -- | ++ |
| 19 | +++ | -- | ++ |
| 20 | +++ | -- | +++ |
| 21 | +++ | -- | +++ |
| 22 | +++ | -- | +++ |
| 23 | +++ | -- | ++ |
| 24 | +++ | -- | ++ |
| 25 | +++ | -- | +++ |
| 26 | +++ | -- | +++ |
| 27 | +++ | -- | +++ |
| 28 | +++ | -- | +++ |
| 29 | +++ | -- | +++ |
| 30 | +++ | -- | +++ |
| 31 | +++ | -- | +++ |
| 32 | +++ | -- | +++ |
| 33 | +++ | -- | +++ |
| 34 | +++ | -- | +++ |
| 35 | +++ | -- | ++ |
| 36 | +++ | -- | +++ |
| 37 | +++ | -- | +++ |
| 38 | +++ | -- | +++ |
| 39 | +++ | -- | ++ |
| 40 | +++ | -- | ++ |
| 41 | +++ | -- | +++ |
| 42 | +++ | -- | +++ |
| 43 | +++ | -- | +++ |
| 44 | +++ | -- | ++ |
| 45 | +++ | -- | + |
| 46 | +++ | -- | ++ |
| 47 | +++ | -- | -- |
| 48 | +++ | -- | -- |
| 49 | +++ | -- | -- |
| 50 | +++ | -- | -- |
| 51 | +++ | -- | -- |
| 52 | +++ | -- | -- |
| 53 | -- | -- | -- |
| 54 | -- | -- | -- |

Legend:
"+" represents a value of ≦10,000 nM
"++" represents a value of ≦1,000 nM
"+++" represents a value of ≦500 nM
"--" indicates the value was not determined The following Preparations and Examples further illustrate the invention and represent typical syntheses of the compounds of Formula I, including any novel compounds, as described generally in the Schemes above. The reagents and starting materials are readily available from commercial suppliers or may be readily synthesized by one of ordinary skill in the art following the general procedures as described herein. Where the synthesis of the compound is not explicitly stated, a reference to a previous Example or representative Scheme describing procedures for the synthesis of the compound is provided. It should be understood that the Preparations and Examples are set forth by way of illustration and not limitation, and that various modifications may be made by one of ordinary skill in the art.

As used herein, the following terms have the meanings indicated: "i.v." refers to intravenously; "p.o." refers to orally; "i.p." refers to intraperitoneally; "eq" or "equiv." Refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "$PPh_3$" refers to triphenylphosphine; "DEAD" refers to diethyl azodicarboxylate; "RT" refers to room temperature; "Pd—C" refers to palladium over carbon; "SAX" refers to strong anion exchange; "SCX" refers to strong cation exchange; $NaBH(Oac)_3$ refers to sodium triacetoxyborohydride; "Bn" refers to benzyl; "$BnNH_2$" refers to benzyl amine; m-CPBA refers to meta-chloroperoxybenzoic acid; $H_2$ refers to hydrogen; "$K_i$" refers to the dissociation constant of an enzyme-antagonist complex and serves as an index of ligand binding; and "$ID_{50}$" and "$ID_{100}$" refer to doses of an administered therapeutic agent which produce, respectively, a 50% and 100% reduction in a physiological response.

Instrumental Analysis:

Unless otherwise indicated, $^1$H NMR spectra are recorded on a either a 300 MHz or 400 MHz Varian spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. Positive and negative electrospray mass spectral data are obtained on a Micromass Platform LCZ equipped with an autosampler. Analytical thin layer chromatography is performed on EM Reagent 0.25-mm silica gel 60-F plates. Visualization is accomplished with UV light. HPLC analysis is performed on an Agilent 1100 Series HPLC using an acetonitrile/0.03M phosphate buffer (80/20) as the mobile phase using an Agilent Eclipse XDB-C8 analytical 4.6×150 mm 5-micron column. Melting points are determined on a Mettler Toledo FP62 melting point apparatus. GC-MS data are obtained on an Agilent HP6890 GC using a HP-5MS (30 m, 0.25 mm i.d., 0.25 µm film) column.

Preparation 1

3-Fluoro-11-methylene-6,11-dihydro-dibenzo[b,e]oxepine

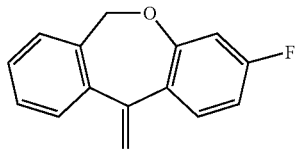

Cool a solution of 3-fluoro-6H-dibenzo[b,e]oxepin-11-one (prepared according to the procedure reported by M Kurokawa, F Sato, Y Masuda, T Yoshida and Y Ochi, *Chem. Pharm. Bull.*, 1991, 39(10), 2564-5273; 11.5 g, 50.5 mmol) and THF (100 mL) to 0° C. under $N_2$. Add dropwise MeMgBr (3.0M in Et2O, 33.7 mL, 101 mmol) this mixture. Warm to room temperature and stir overnight. Cool to 0° C. and quench very carefully (exotherm) with HCl (4.00 M in dioxane, 30 mL). Warm to room temperature and stir for 30 min. Dilute reaction mixture with water (70 mL) and extract into ethyl acetate (three 100 mL portions). Dry ($MgSO_4$), filter, and concentrate organics to a brown solid. Purify crude product on a 100 g plug of silica gel, eluting with hexanes to afford 9.26 g (81%) of the title compound as a yellow solid. MS [EI] 226; HPLC shows 90% purity.

Preparation 2

11-Bromomethylene-3-fluoro-6,11-dihydro-dibenzo[b,e]oxepine

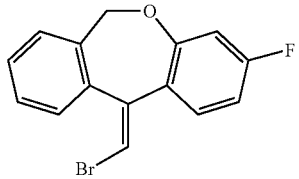

Dissolve 3-fluoro-11-methylene-6,11-dihydro-dibenzo[b,e]oxepine (8.23 g, 36.4 mmol) in $CH_2Cl_2$ (200 mL), then add DMAP.$HBr_3$ (15.8 g, 43.7 mmol). Once DMAP.$HBr_3$ has dissolved, quench excess bromine with saturated aqueous $Na_2SO_3$ (50 mL). Dilute with water (50 mL) and extract with $CH_2Cl_2$ (three 10 mL portions). Dry ($MgSO_4$), filter, and concentrate organics to afford a yellow solid. Recrystallize from warm MeOH (200 mL) to afford a 97:3 E/Z mixture (HPLC) of the title compound. MS [EI] 304, 306.

Preparation 3

2-(4-Bromo-2-nitro-phenylamino)-2-methyl-propan-1-ol

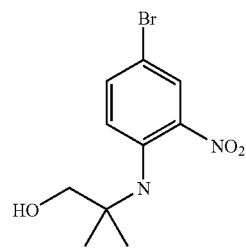

As shown in Scheme ??, mix 5-bromo-2-fluoronitrobenzene (11.2 g, 50.5 mmol) and 2-amino-2-methyl-1-propanol (10.5 mL, 110 mmol) in THF (120 mL). Heat at reflux for 48 h and then cool to room temperature. Remove most of the THF under reduced pressure and then partition the residue between water and EtOAc. Wash the organic layer a second time with water and the dry (MgSO4) and concentrate to give an orange solid. Triturate the solid with hexane (200 mL) and dry to yield 12.95 g (89%) title compound. MS (es) 288 (M−1). HPLC (ISO80-10M) t=2.67 (100%).

Preparation 4

Toluene-4-sulfonic acid 2-(4-bromo-2-nitro-phenylamino)-2-methyl-propyl ester

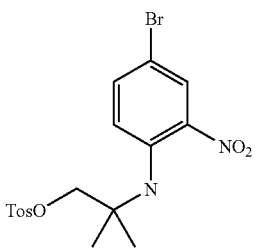

In dichloromethane (300 mL), mix 2-(4-bromo-2-nitrophenylamino)-2-methylpropan-1-ol (23.1 g, 9.7 mmol), p-toluenesulfonic anhydride (31.3 g, 11.96 mmol), pyridine (22 mL, 272 mmol) and DMAP (2.9 g, 24 mmol). Stir overnight at room temperature and then shake with water/methylene chloride. Dry (Na2SO4) and concentrate to give 34.7 g (98%) title compound as an orange solid. MS (es) 443, 445 (M+1). HPLC (ISO80-10M) t=4.45 (98%).

Preparation 5

(4-Bromo-2-nitro-phenyl)-(1,1-dimethyl-2-morpholin-4-yl-ethyl)-amine

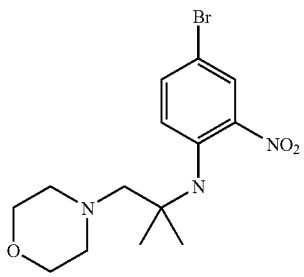

In a 250 mL flask, mix toluene-4-sulfonic acid 2-(4-bromo-2-nitro-phenylamino)-2-methyl-propyl ester (19.5 g, 44 mmol) and morpholine (50 mL). Heat at 100-110° C. for 2 days. Follow the progress of the reaction by HPLC. Cool the reaction and partition between water and EtOAc. Wash the organic layer with water (2×), dry (MgSO4) and concentrate to give 14 g dark oil. Recrystallize from heptane (400 mL) to give 11 g that is 80% pure by HPLC. Recrystallize a second time to give 6.6 g (42%) orange crystals; MS (es) 358, 360 (M+1), HPLC (ISO80-10M) t=3.17 (94%).

Preparation 6

4-Bromo-N1-(1,1-dimethyl-2-morpholin-4-yl-ethyl)-benzene-1,2-diamine

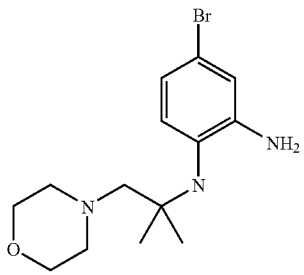

Mix (4-bromo-2-nitro-phenyl)-(1,1-dimethyl-2-morpholin-4-yl-ethyl)-amine (4 g, 11.1 mmol) and 5% Pt/C(S) (100 mg) in EtOAc (215 mL) and place under 60 psi hydrogen for 18 h. Filter and concentrate to give 3.76 (100%) title compound as a pale yellow oil; MS (es) 328, 330 (M+1), HPLC (ISO80-10M) t=1.57 (95%).

Preparation 7

5-Bromo-1-(1,1-dimethyl-2-morpholin-4-yl-ethyl)-1,3-dihydro-benzoimidazol-2-one

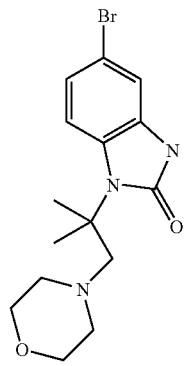

Mix 4-bromo-N1-(1,1-dimethyl-2-morpholin-4-yl-ethyl)-benzene-1,2-diamine (3.76 g, 11.5 mmol), triethylamine (4.6 mL, 34.4 mmol) in THF (150 mL). Cool to 0° C. and carefully add solid triphosgene (2.0 g, 6.9 mmol). Allow the reaction to warm to room temperature and stir for 18 h. Cautiously quench the reaction with aqueous K2CO3 and extract into EtOAc. Dry (MgSO4) and concentrate to give 3.4 g yellow solid. Purify by column chromatography using 3% 3N NH3 in MeOH/methylene chloride to give 2.25 g (55%) title compound as a white solid, MS (es) 354, 356 (M+1), 352, 354 (M−1). HPLC(ISO80-10M) t=1.55.

Preparation 8

1-(1,1-Dimethyl-2-morpholin-4-yl-ethyl)-5-(4,4,5,5-tetramethyl-[1,3,2]dioxaborolan-2-yl)-1,3-dihydro-benzoimidazol-2-one

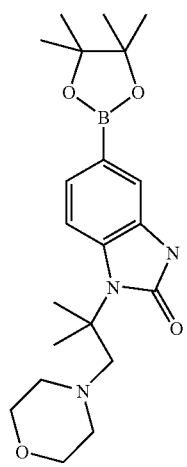

Mix 5-bromo-1-(1,1-dimethyl-2-morpholin-4-yl-ethyl)-1,3-dihydro-benzoimidazol-2-one (2.68 g, 7.55 mmol), bis(pinacaloto)diborane (2.11 g, 8.3 mmol), tricyclophosphine (296 mg, 1.06 mmol) and KOAc (2.22 g, 22.65 mmol) in dry DMSO (40 mL). Sparge with nitrogen for 10 min and then add tris(benzylideneacetone)dipalladium (415 mg, 0.45 mmol). Under a blanket of nitrogen, heat the reaction at 95°

C. for 18 h. Cool the reaction and shake with water/EtOAc. Wash the organic layer with water (2×), dry (MgSO4) and concentrate to give 2.7 g light tan foam. HPLC (ISO80-10M) shows t=1.65 (58%) and MS (es) 402 (M+1), 400 (M−1). Use the material without further purification.

Example 1

1-(1,1-Dimethyl-2-morpholin-4-yl-ethyl)-5-(3-fluoro-6H-dibenzo[b,e]oxepin-11-ylidenemethyl)-1,3-dihydro-benzoimidazol-2-one, E isomer

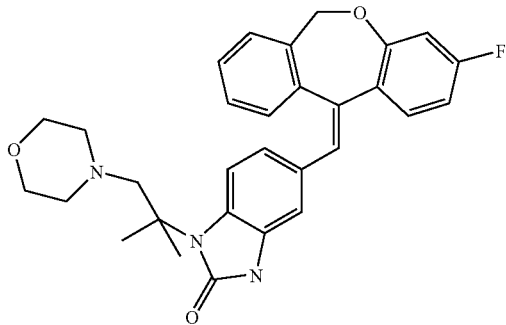

Mix 1-(1,1-dimethyl-2-morpholin-4-yl-ethyl)-5-(4,4,5,5-tetramethyl-[1,3,2]dioxaborolan-2-yl)-1,3-dihydro-benzoimidazol-2-one (900 mg of 60% purity, 1.34 mmol), 11-bromomethylene-3-fluoro-6,11-dihydro-dibenzo[b,e]oxepine (E-isomer, 520 mg, 1.7 mmol), 2N Na2CO3 (4 mmol) in dioxane (10 mL). Sparge with nitrogen for 10 min and then add tetrakistriphenylphosphine Pd (0) (98 mg, 0.08 mmol) and heat at 90-100° C. 5 days. Cool the reaction and shake with water/EtOAc. Dry (MgSO4) and concentrate to give 1.05 g crude product. Purify by column chromatography using 2% 2N NH3 in MeOH/methylene chloride to give 400 mg (80%) title compound as an off-white solid. MS (es) 500 (M+1), 498 (M−1); HPLC (ISO80-10M) t=1.95 min (100%); ¹NMR (CDCl3) 8.17 (s, 1H), 7.49 (t, 1H, J=7.5 Hz), 7.46 (d, 1H, J=7.0 Hz), 7.37 (t, 1H, J=7.0 Hz), 7.26 (t, 1H, J=7.5 Hz), 7.14 (d, 1H, J=7.5 Hz), 6.91 (d, 1H, J=8.5 Hz), 6.89 (s, 1H), 6.81 (d, 1H, J=7.5 Hz), 6.70 (td, 1H, J=11.7, 4.1 Hz), 6.66 (s, 1H), 6.56 (dd, 1H, J=10.1, 2.6 Hz), 6.03-4.76 (br d, 2H), 3.85-3.70 (m, 6H), 2.73 (t, 4H, J=4.2 Hz), 1.13 (s, 6H).

Example 2

5-(3,7-Difluoro-6H-dibenzo[b,e]oxepine-11-ylidenemethyl)-1-(1-methyl-piperidin-4-yl)-1,3-dihydro-benzoimidazol-2-one, E-isomer

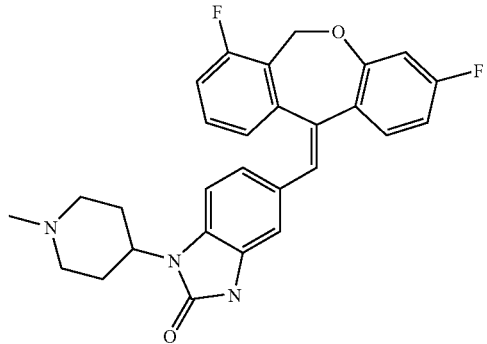

Use a procedure similar to that of Example 1 and procedures as described in Scheme IV to prepare the title compound in 37% yield. MS (es) 474 (M+1); HPLC (ISO80-10M) t=1.89 min (97%); ¹NMR (CD3OD, 400 MHz) δ: 1.76 (d, 2H), 2.23 (t, 2H), 2.36 (s, 3H), 2.45 (dq, 2H), 3.03 (d, 2H), 4.26 (m, 1H), 5.42 (broad s, 2H), 6.53 (dd, 1H), 6.68 (s, 1H), 6.72 (t, 1H), 6.82 (d, 1H), 6.88 (d, 1H), 7.00 (s, 1H), 7.12 (t, 1H), 7.20 (m, 2H), 7.52 (t, 1H).

Example 3

5-(3-Fluoro-6H-dibenzo[b,e]oxepin-11-ylidenemethyl)-1-(1-methyl-piperidin-4-yl)-1,3-dihydro-benzoimidazol-2-one, E isomer

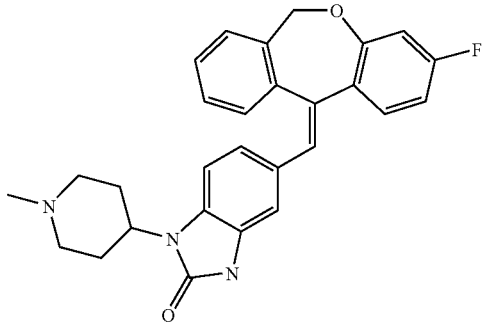

Use a procedure similar to that of Example 1 and procedures as described in Scheme IV to prepare the title compound in 55% yield. MS (es) 456 (M+1); ¹NMR (CD3OD, 400 MHz) δ: 1.76 (d, 2H), 2.25 (t, 2H), 2.36 (s, 3H), 2.46 (dq, 2H), 3.03 (d, 2H), 4.25 (m, 1H), 6.50 (dd, 1H), 6.65 (s, 1H), 6.68 (t, 1H), 6.83 (d, 1H), 6.95 (s, 1H), 7.02 (d, 1H), 7.18 (d, 1H), 7.21 (t, 1H), 7.36 (t, 1H), 7.51 (m, 2H).

Example 4

5-(3,8-Difluoro-6H-dibenzo[b,e]oxepin-11-ylidenemethyl)-1-(1-methyl-piperidin-4-yl)-1,3-dihydro-benzoimidazol-2-one, E isomer

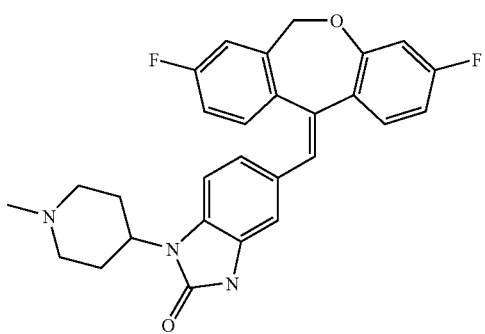

Use a procedure similar to that of Example 1 and procedures as described in Scheme IV to prepare the title compound in 60% yield. MS (es) 474 (M+1); HPLC (ISO80-10M) t=1.86 min (99%); ¹NMR (CD3OD, 400 MHz) δ: 1.78 (d, 2H), 2.25 (t, 2H), 2.38 (s, 3H), 2.48 (dq, 2H), 3.04 (d, 2H), 4.28 (m, 1H), 6.53 (d, 1H), 6.68 (s, 1H), 6.73 (t, 1H), 6.88 (d, 1H), 6.99-7.08 (m, 3H), 7.21 (d, 1H), 7.33 (d, 1H), 7.58 (t, 2H).

Example 5

5-(3,8-Difluoro-6H-dibenzo[b,e]oxepin-11-ylidenemethyl)-1-(1-ethyl-pyrrolidin-3-yl)-1,3-dihydro-benzoimidazol-2-one, HOAc salt, E isomer, chiral

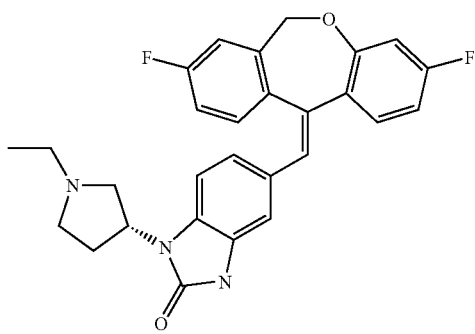

Stir 5-(3,8-difluoro-6H-dibenzo[b,e]oxepin-11-ylidenemethyl)-1-pyrrolidin-3-yl-1,3-dihydro-benzoimidazol-2-one hydrochloride (500 mg, 1.04 mmol) and acetaldehyde (87 ul, 1.56 mmol, 1.50 equivalents) in 1,2-dichloroethane under nitrogen at room temperature for 20 minutes. Add sodium triacetoxyborohydride (441 mg, 2.08 mmol, 2.00 equivalents) portionwise and stir at room temperature under nitrogen overnight. After the reaction is complete by LC-MS, purify by silica column chromatography eluting with 10% methanol in dichloromethane to obtain the title compound as a white solid (389 mg, 79%). MS (es) 474 (M+1); HPLC (ISO80-10M) t=1.86 min (99%); $^1$NMR (CDCl3, 400 MHz) δ: 1.25 (t, 3H), 2.10 (s, 3H, acetate), 2.33 (m, 1H), 2.41 (m, 1H), 2.77-3.02 (m, 3H), 3.18-3.28 (m, 3H), 4.93 (broad s, 1H), 5.16 (m, 1H), 5.7 (broad s, 1H), 6.58 (dd, 1H), 6.68 (s, 1H), 6.71 (t, 1H), 6.81 (d, 1H), 6.90-6.98 (m, 2H), 7.05 (m, 1H), 7.21 (d, 1H), 7.25 (s, 1H), 7.48 (t, 2H), 9.17 (broad s, 1H, NH).

Table II, below, provides yet, additional compounds synthesized according to procedures as described generally in the Schemes I-IV above and more particularly as described in Preparations 1-8 and Examples 1-5.

TABLE II

| Example No. | Structure | MS Data | HPLC Data |
|---|---|---|---|
| 6 | 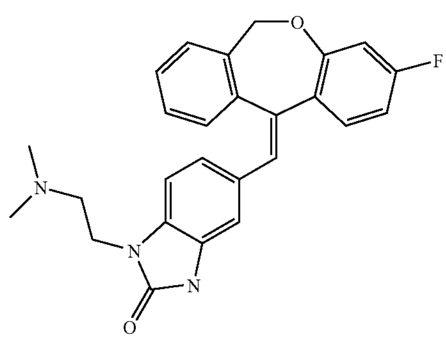 | ES 430 (+) 428 (−) | ISO80 98% |
| 7 | 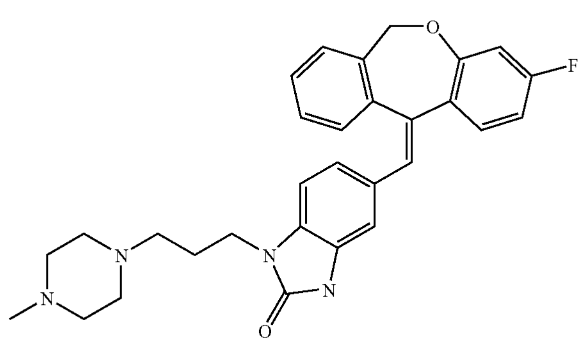 | ES 499 (+) 497 (−) | ISO80 96% |

TABLE II-continued

| Example No. | Structure | MS Data | HPLC Data |
|---|---|---|---|
| 8 | 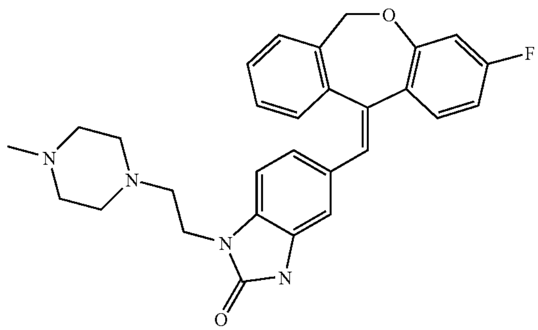 | ES 485 (+) 483 (−) | ISO80 96% |
| 9 | 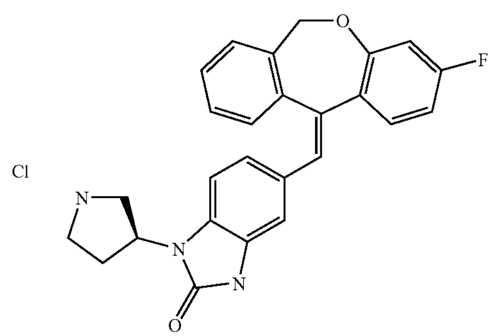 | ES 428 (+) 426 (−) | ISO80 100% |
| 10 | Chiral | ES 486 (+) 484 (−) | ISO80 100% |
| 11 | Chiral | ES 486 (+) 484 (−) | ISO80 98% |

TABLE II-continued

| Example No. | Structure | MS Data | HPLC Data |
|---|---|---|---|
| 12 | 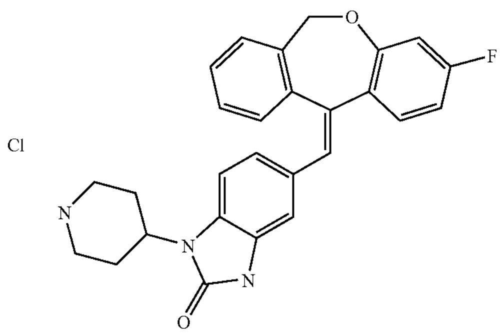 | ES 442 (+) 440 (−) | ISO80 100% |
| 13 | 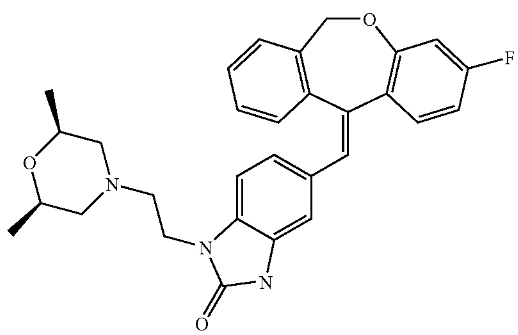 | ES 500 (+) 498 (−) | ISO80 98% |
| 14 | 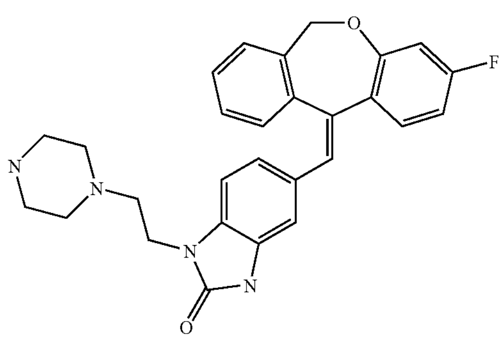 | ES 471 (+) 469 (−) | ISO80 100% |
| 15 | 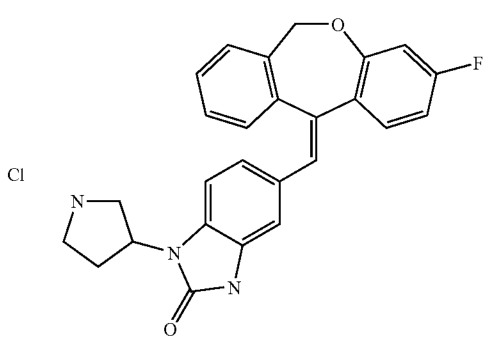 | 428 (+) | ISO80 100% |

TABLE II-continued
| Example No. | Structure | | MS Data | HPLC Data |
|---|---|---|---|---|
| 16 | 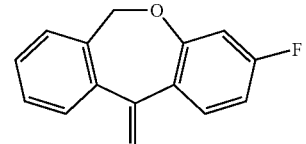 | | 428 (+) | ISO80 99% |
| 17 | 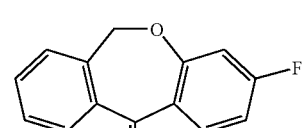 | | ES 414 (+) | NA |
| 18 | 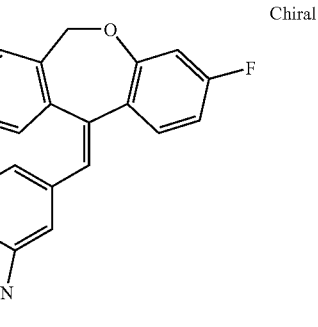 | Chiral | ES 442 (+) 440 (−) | ISO80 98% |
| 19 | 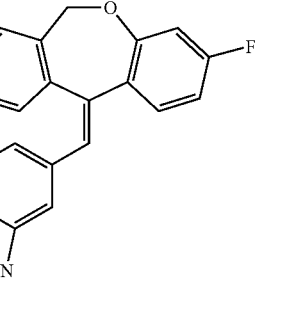 | Chiral | ES 442 (+) | ISO80 99% |

TABLE II-continued

| Example No. | Structure | | MS Data | HPLC Data |
|---|---|---|---|---|
| 20 | 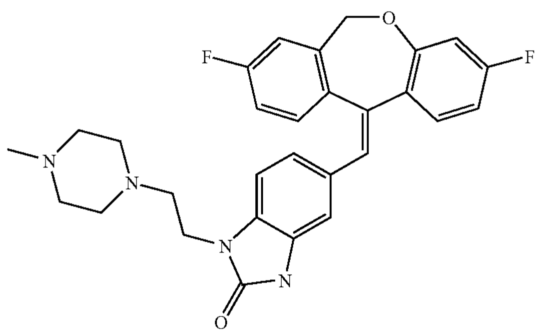 | | ES 503 (+) | ISO80 96% |
| 21 | 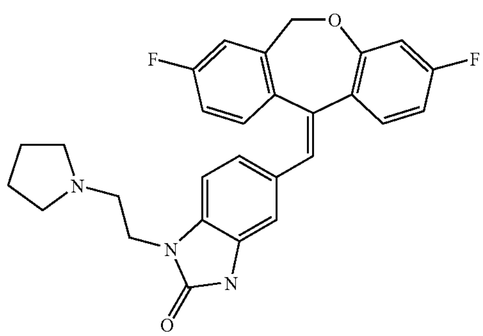 | | ES 474 (+) 472 (−) | ISO80 96% |
| 22 | 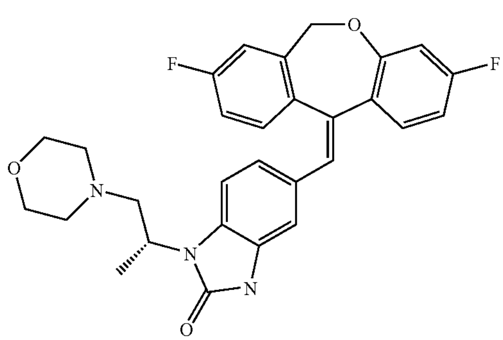 | Chiral | ES 504 (+) 502 (−) | ISO80 99% |
| 23 | 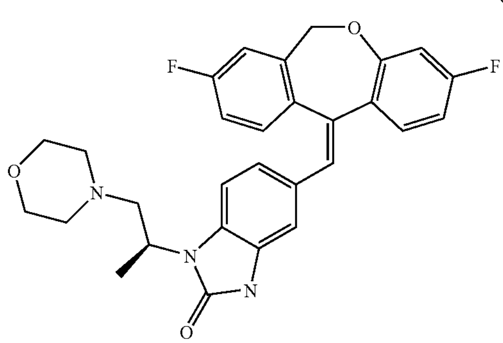 | Chiral | ES 504 (+) 502 (−) | ISO80 99% |

TABLE II-continued
| Example No. | Structure | MS Data | HPLC Data |
|---|---|---|---|
| 24 | 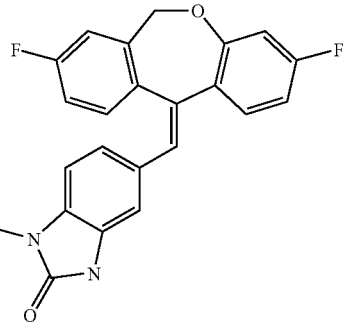 | ES 518 (+) 516 (−) | ISO80 100% |
| 25 | 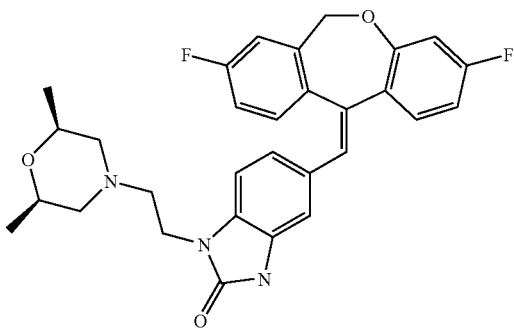 | ES 518 (+) 516 (−) | ISO80 98% |
| 26 | 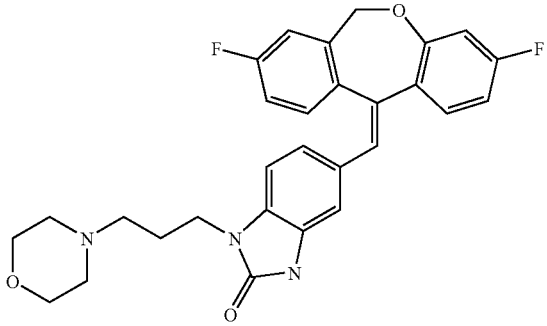 | ES 504 (+) 502 (−) | ISO80 100% |
| 27 | 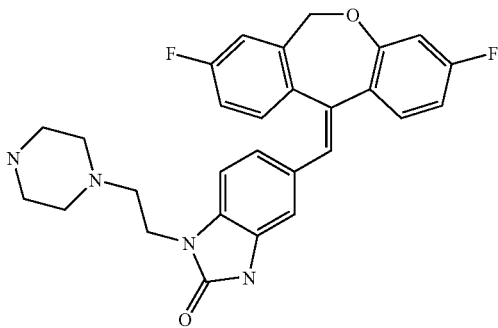 | ES 471 (+) 469 (−) | ISO80 100% |

TABLE II-continued
| Example No. | Structure | MS Data | HPLC Data |
|---|---|---|---|
| 28 | 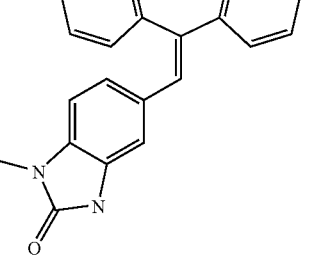 | ES 460 (+) 458 (−) | ISO80 99% |
| 29 | 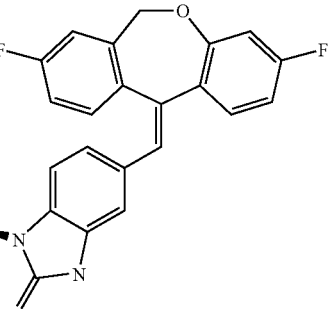 | ES 446 (+) 444 (−) | ISO80 99% |
| 30 | 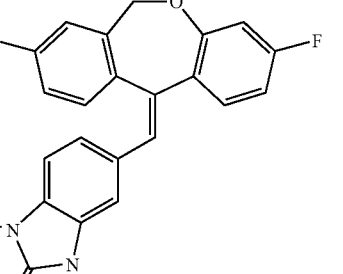 | ES 432 (+) 430 (−) | NA |
| 31 | 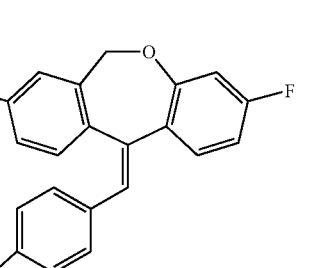 | ES 446 (+) | ISO80 100% |

TABLE II-continued

| Example No. | Structure | | MS Data | HPLC Data |
|---|---|---|---|---|
| 32 | 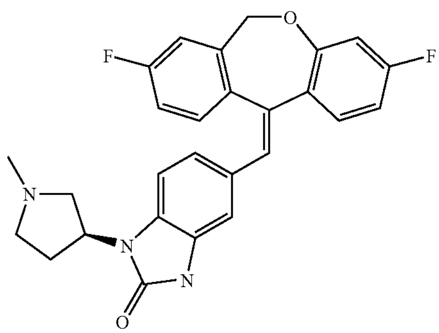 | Chiral | ES 460 (+) | ISO80 99% |
| 33 | 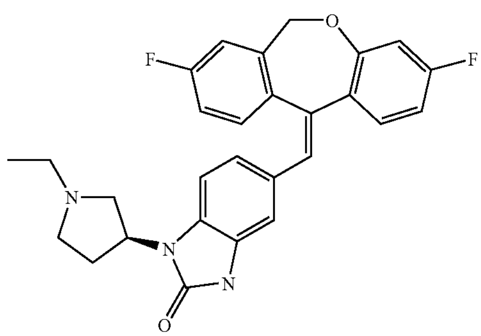 | Chiral | 474 (+) | ISO80 98% |
| 34 | 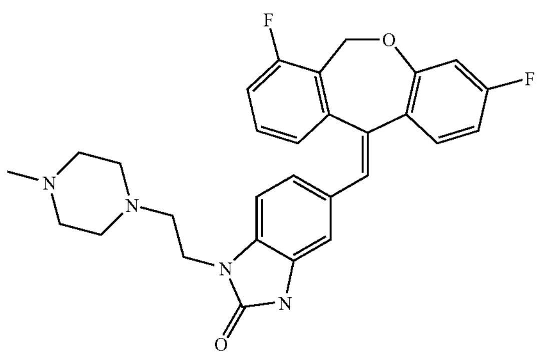 | | ES 503 (+) 501 (−) | ISO80 98% |
| 35 | 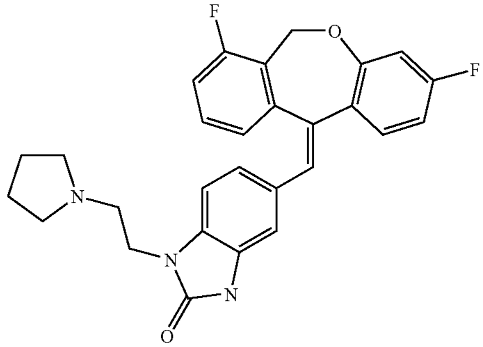 | | ES 474 (+) 472 (−) | ISO80 100% |

TABLE II-continued

| Example No. | Structure | | MS Data | HPLC Data |
|---|---|---|---|---|
| 36 | 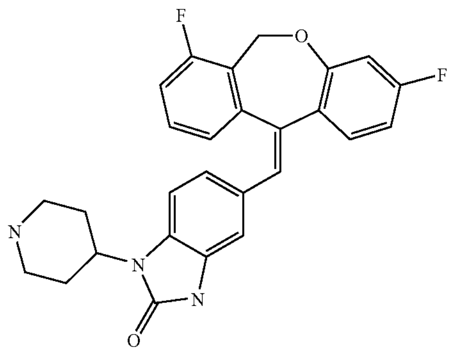 | | ES 460 (+) 458 (−) | NA |
| 37 | 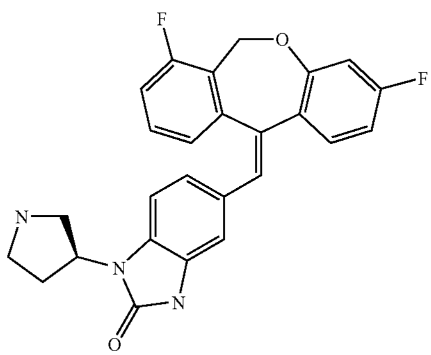 | | ES 446 (+) | ISO80 95% |
| 38 | 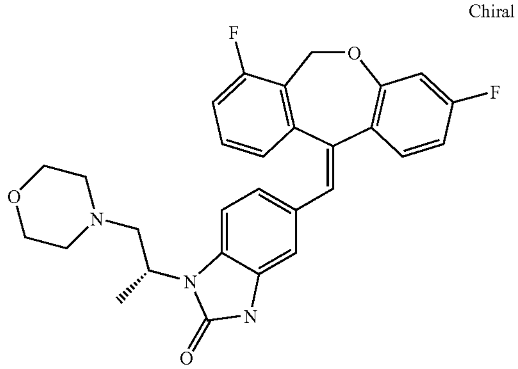 | Chiral | ES 504 (+) 502 (−) | ISO80 100% |
| 39 | 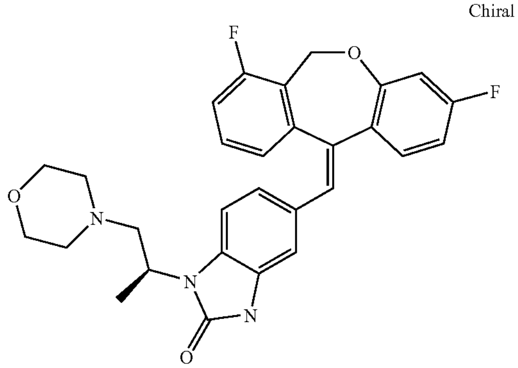 | Chiral | ES 504 (+) 502 (−) | ISO80 100% |

TABLE II-continued

| Example No. | Structure | MS Data | HPLC Data |
|---|---|---|---|
| 40 | 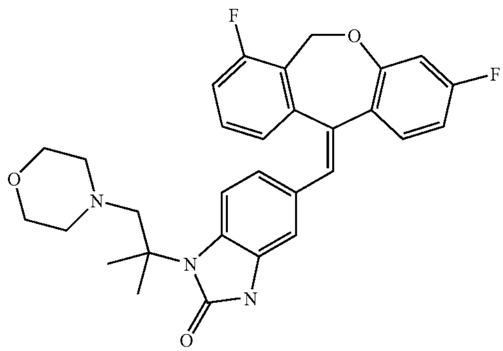 | ES 518 (+) 516 (−) | ISO80 99% |
| 41 | 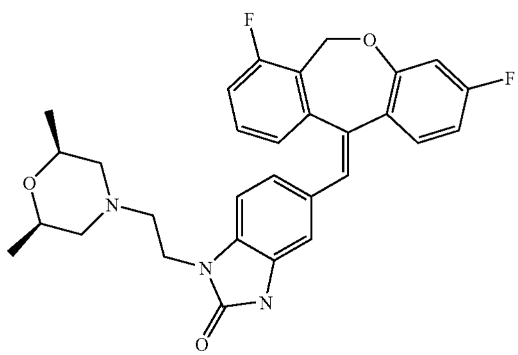 | ES 518 (+) 516 (−) | ISO80 99% |
| 42 | 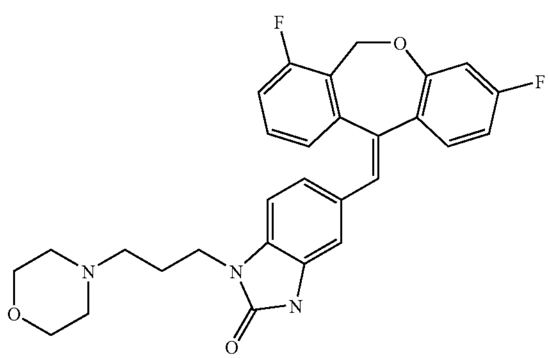 | ES 504 (+) 502 (−) | ISO80 97% |
| 43 | 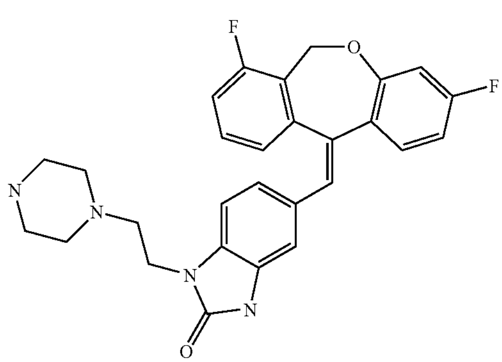 | ES 489 (+) 487 (−) | ISO80 100% |

TABLE II-continued

| Example No. | Structure | | MS Data | HPLC Data |
|---|---|---|---|---|
| 44 | 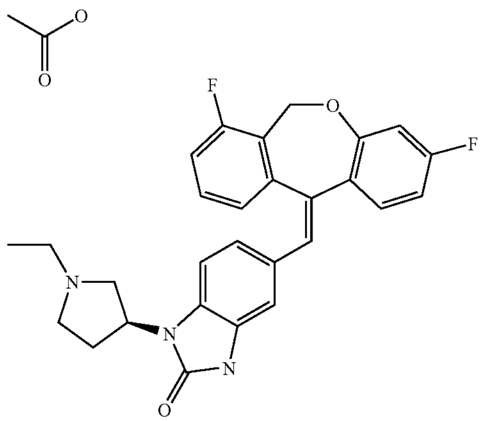 | Chiral | 474 (+) | ISO80 96% |
| 45 | 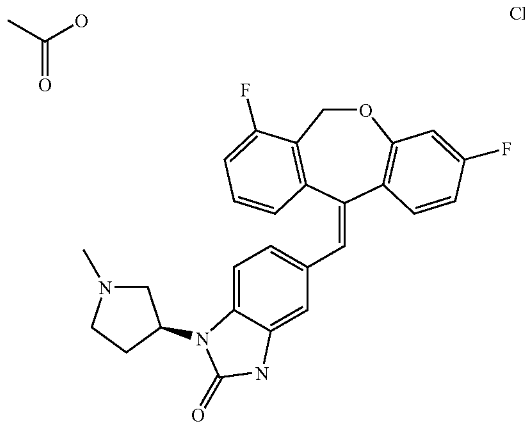 | Chiral | 460 (+) | ISO80 95% |
| 46 | 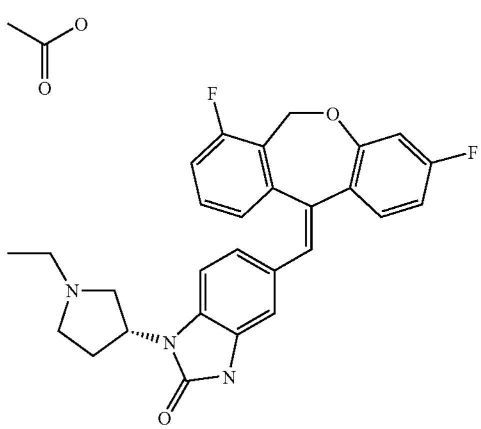 | Chiral | ES 474 (+) 472 (−) | ISO80 98% |

TABLE II-continued

| Example No. | Structure | MS Data | HPLC Data |
|---|---|---|---|
| 47 | Chiral | ES 460 (+) | NA |
| 48 | 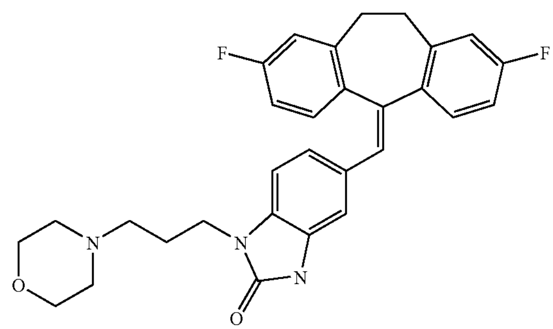 | ES 502 (+) 500 (−) | ISO80 98% |
| 49 | 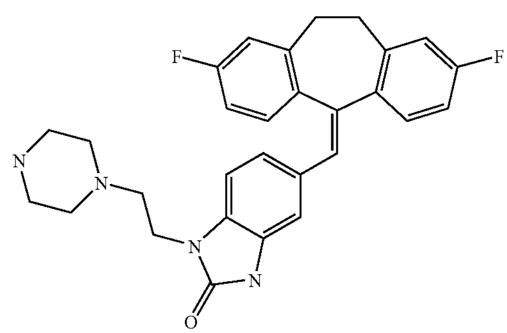 | ES 487 (+) 485 (−) | ISO80 96% |
| 50 | 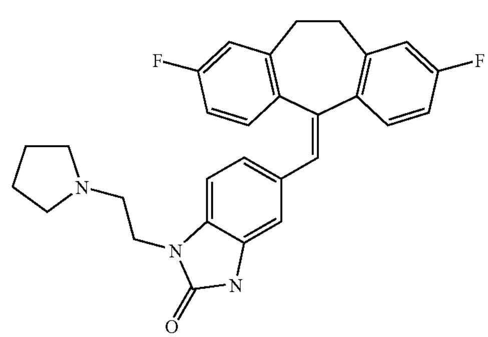 | ES 472 (+) 470 (−) | ISO80 97% |

TABLE II-continued

| Example No. | Structure | MS Data | HPLC Data |
|---|---|---|---|
| 51 | 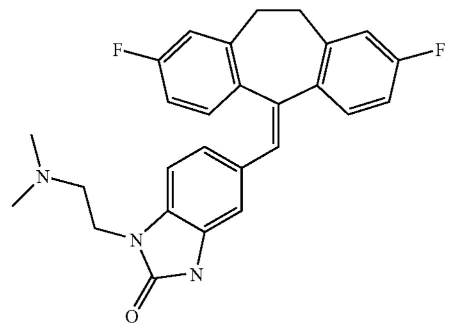 | ES 446 (+) 444 (−) | ISO80 98% |
| 52 | 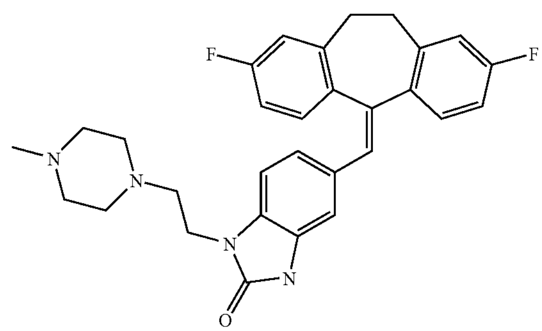 | ES 501 (+) 499 (−) | ISO80 100% |
| 53 | 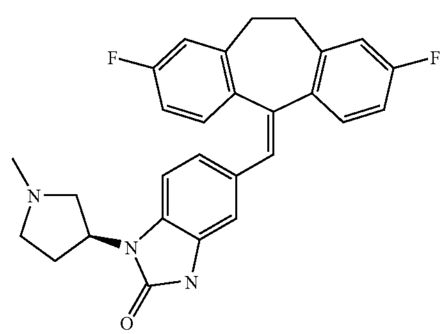 | ES 458 (+) | ISO80 98.4% |
| 54 | 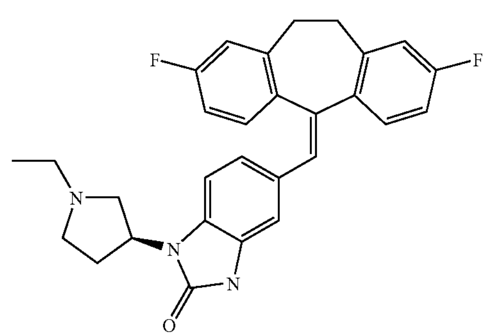 | ES 472 (+) | ISO80 98.6% |

TABLE II-continued

| Example No. | Structure | MS Data | HPLC Data |
|---|---|---|---|
| 55 | 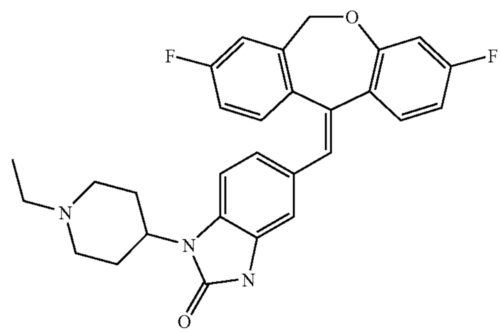 | ES 488 (+) 486 (−) | ISO80 97.4% |
| 56 | 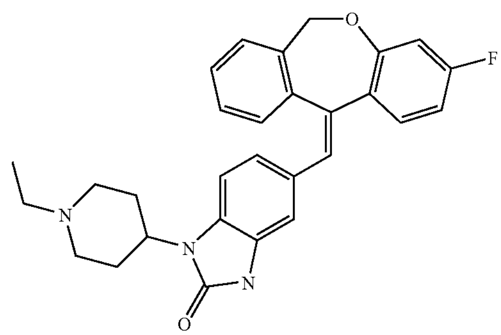 | ES 470 (M + 1) | ISO80 98.5% |
| 57 | 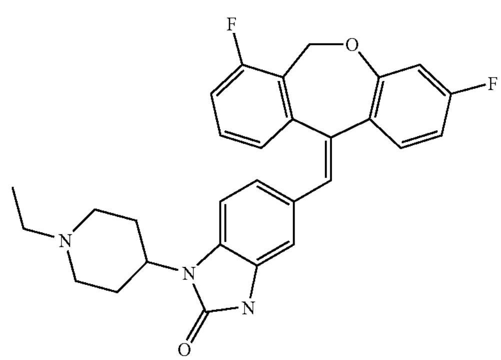 | ES 488 (+) 486 (−) | ISO80 99.3% |
| 58 | 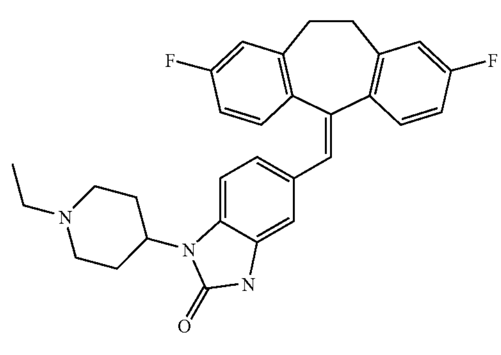 | ES 486 (M + 1) | ISO80 99% |

TABLE II-continued
| Example No. | Structure | | MS Data | HPLC Data |
|---|---|---|---|---|
| 59 | 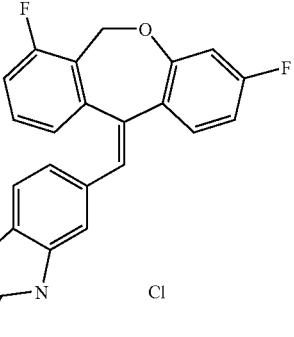 | | ES 460 (+) 458 (−) | ISO80 100% @ 1.84 min |
| 60 | 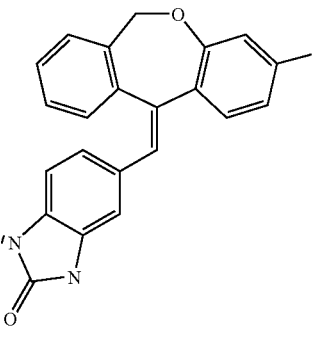 | Chiral | ES 456 (+) | ISO80 99% |
| 61 | 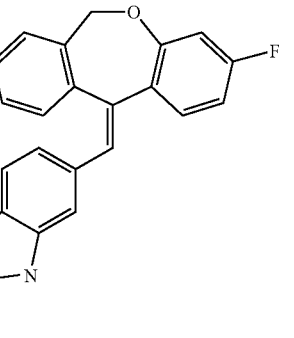 | Chiral | ES 442 (+) | ISO80 98% |

We claim:

1. A compound of the formula:

Formula I

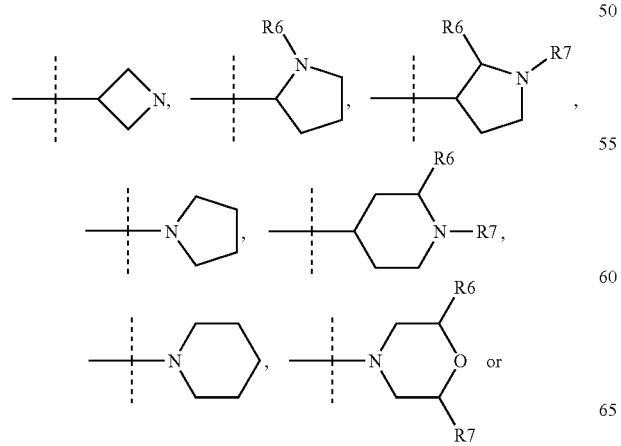

wherein,

Y represents $CH_2$ or O;

R1 and R2 each independently represent hydrogen or fluoro

R3 represents a group of the formula:

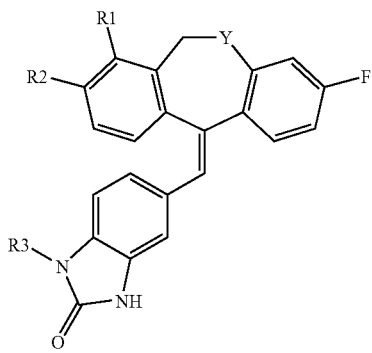   or   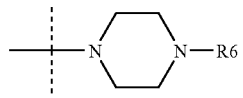

wherein Z represents $(CH_2)_n$ or $—CR4R5-CH2-$;

n represents 0-3; and

Het represents a group of the formula:

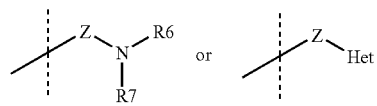

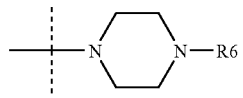

R4 and R5 each independently represent at each occurrence hydrogen or methyl;

R6 and R7 each independently represent at each occurrence hydrogen, methyl, or ethyl;

provided Formula I does not represent a compound selected from the group consisting of

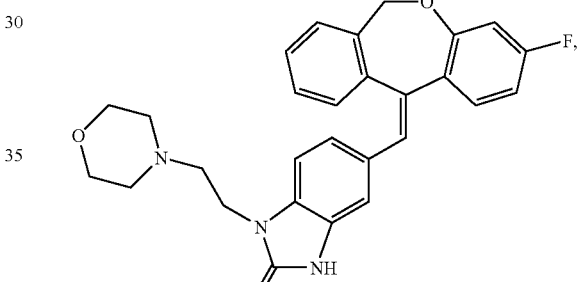

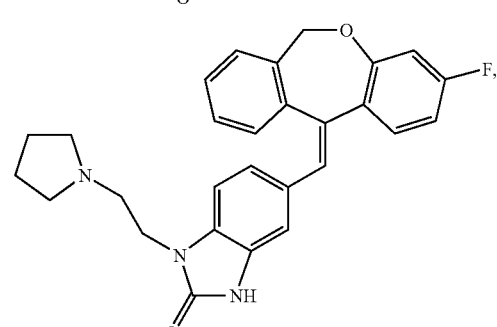

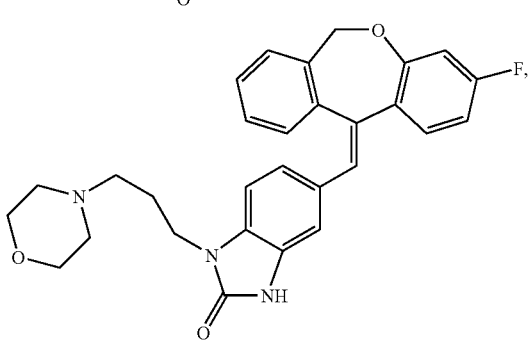

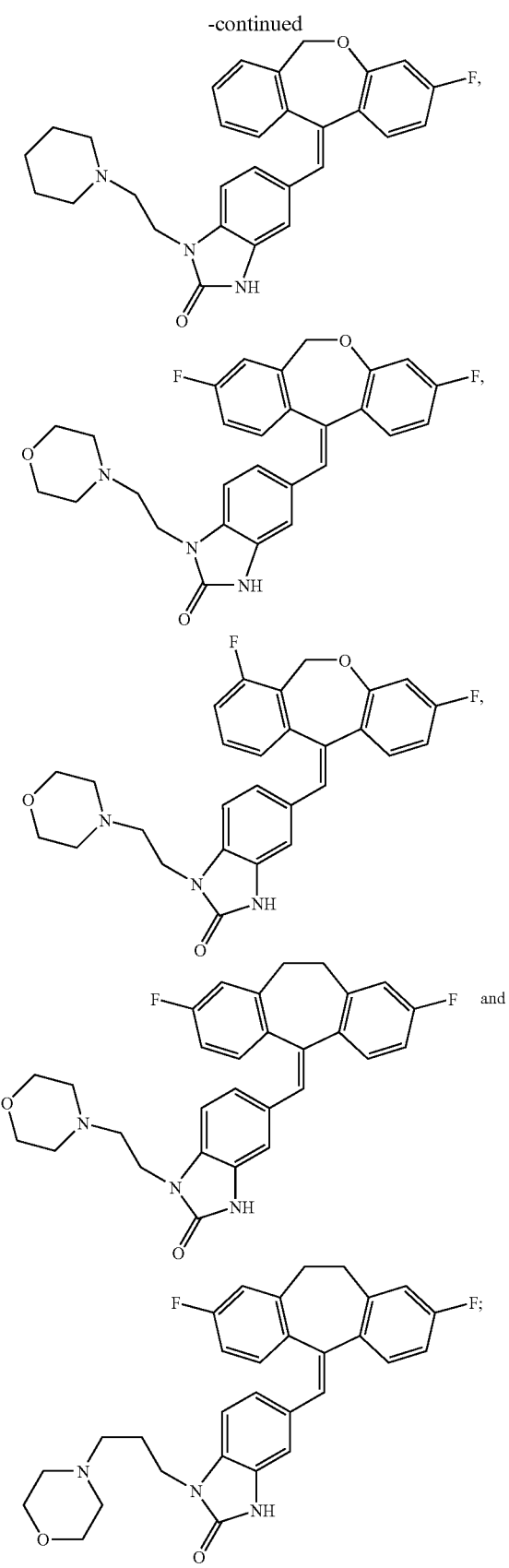

or a pharmaceutically acceptable salt thereof.

2. The compound according to claim 1 wherein $R^1$ represents hydrogen.

3. The compound according to claim 1 wherein $R^1$ represents fluoro.

4. The compound according to claim 1 wherein $R^2$ represents hydrogen.

5. The compound according to claim 1 wherein $R^2$ represents fluoro.

6. The compound according to claim 1 wherein $R^3$ represents a group of the formula:

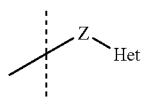

wherein Z represents (CH2)n or —CR4R5-CH2-;
n represents 0-3; and
Het represents a group of the formula:

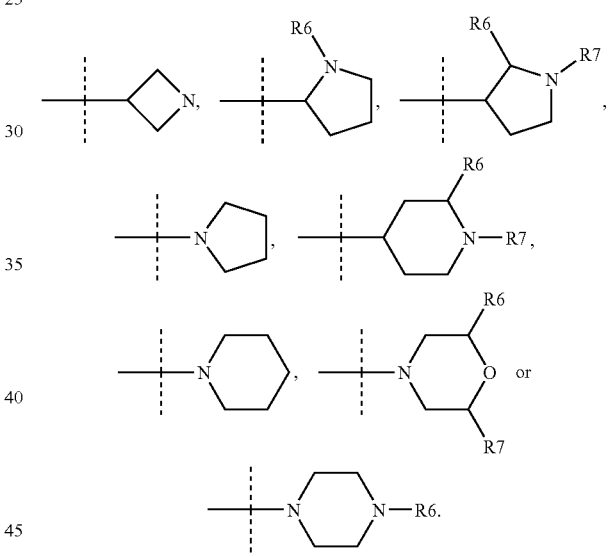

7. The compound according to claim 6 wherein Het represents a group of the formula:

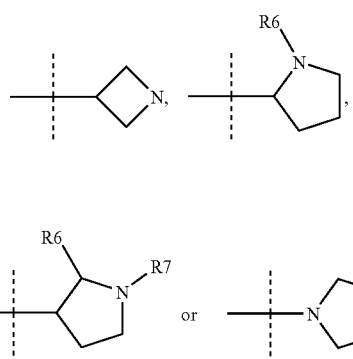

8. The compound according to claim 6 wherein Het represents a group of the formula:

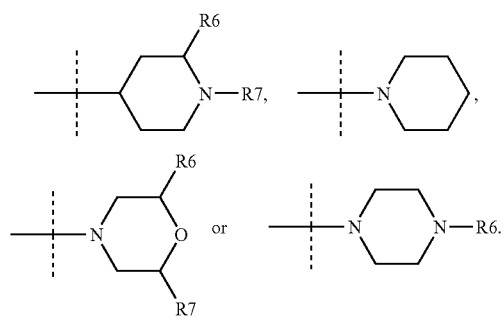

9. The compound according to claim 6 wherein $R^3$ represents a group of the formula:

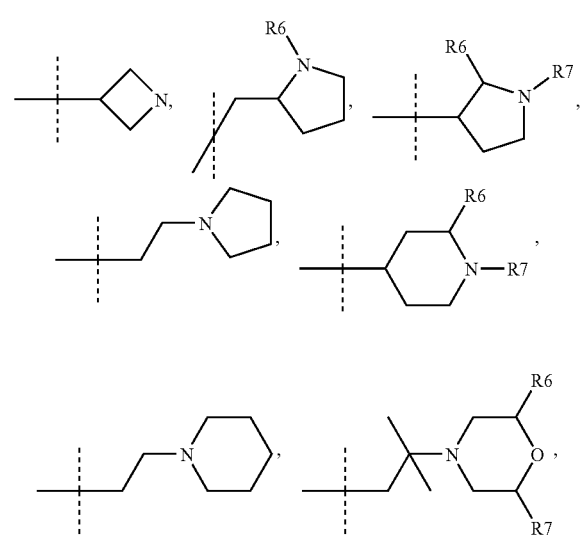

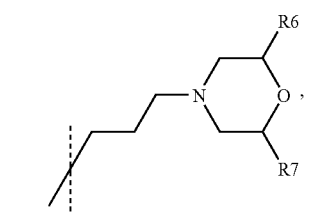

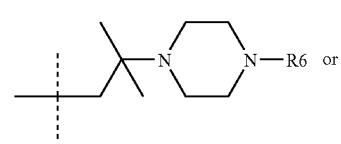

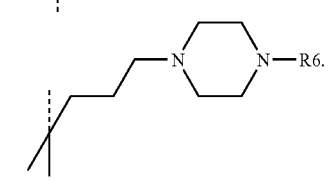

10. The compound according to claim 9 wherein $R^3$ represents a group of the formula:

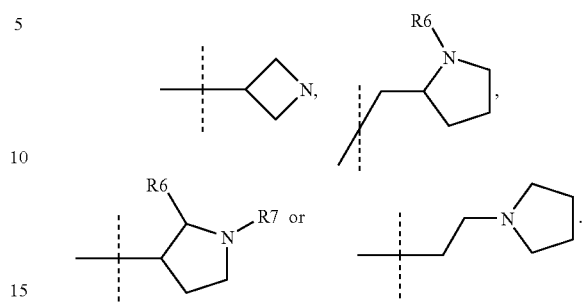

11. The compound according to claim 9 wherein $R^3$ represents a group of the formula:

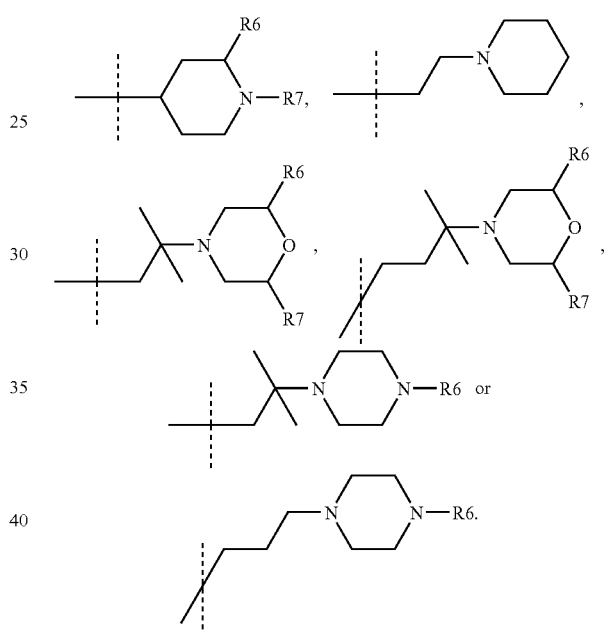

12. The compound according to claim 1 wherein $R^3$ represents a group of the formula:

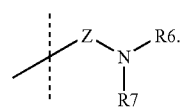

13. The compound according to claim 12 wherein $R^3$ represents a group of the formula:

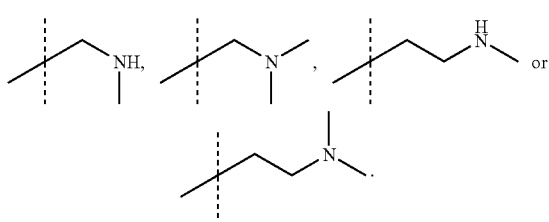

14. A pharmaceutical composition comprising the compound according to claim 1 in combination with a pharmaceutically acceptable carrier, diluent, or excipient.

15. The compound according to claim 1 selected from the group consisting of 5-(3,7-Difluoro-6H-dibenzo[b,e]oxepine-11-ylidenemethyl)-1-(1-methyl-piperidin-4-yl)-1,3-dihydro-benzoimidazol-2-one, E-isomer; 5-(3-Fluoro-6H-dibenzo[b,e]oxepin-11-ylidenemethyl)-1-(1-methyl-piperidin-4-yl)-1,3-dihydro-benzoimidazol-2-one, E isomer; 5-(3,8-Difluoro-6H-dibenzo[b,e]oxepin-11-ylidenemethyl)-1-(1-methyl-piperidin-4-yl)-1,3-dihydro-benzoimidazol-2-one, E isomer; (R)-5-(3-fluoro-6H-dibenzo[b,e]oxepin-11-ylidenemethyl)-1-[1-(1-methyl-2-morpholin-4-yl-ethyl)-piperidin-4-yl]-1,3-dihydro-benzoimidazol-2-one, E isomer; and (R)-5-(3,7-difluoro-6H-dibenzo[b,e]oxepin-11-ylidenemethyl)-1-(1-methyl-pyrrolidin-3-yl)-1,3-dihydro-H-benzoimidazol-2-one, E isomer.

* * * * *

SEQUENCE LISTING
<160> NUMBER OF SEQ ID NOS: 2
<210> SEQ ID NO 1
<211> LENGTH: 15
<212> TYPE: DNA
<213> ORGANISM: Artificial Sequence
<220> FEATURE:
<223> OTHER INFORMATION: Synthetic construct
<400> SEQUENCE: 1
tgtacaggat gttct    15
<210> SEQ ID NO 2
<211> LENGTH: 15

-continued

```
<212> TYPE: DNA
<213> ORGANISM: Artificial Sequence
<220> FEATURE:
<223> OTHER INFORMATION: Synthetic construct

<400> SEQUENCE: 2
ggttcttgga gtact                                                    15
```